United States Patent
Linsley et al.

(10) Patent No.: US 6,641,809 B1
(45) Date of Patent: Nov. 4, 2003

(54) METHOD OF REGULATING CELLULAR PROCESSES MEDIATED BY B7 AND CD28

(75) Inventors: Peter S. Linsley, Seattle, WA (US); Jeffrey A. Ledbetter, Seattle, WA (US); Nitin K. Damle, Renton, WA (US); William Brady, Bothell, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/219,200

(22) Filed: Mar. 29, 1994

Related U.S. Application Data

(63) Continuation of application No. 07/722,101, filed on Jun. 27, 1991, now abandoned, which is a continuation-in-part of application No. 07/547,980, filed on Jul. 2, 1990, now abandoned, which is a continuation-in-part of application No. 07/498,949, filed on Mar. 26, 1990, now abandoned.

(51) Int. Cl.[7] .................... A61K 38/17; C07K 14/705; C12N 15/12; C12N 15/63

(52) U.S. Cl. .................... 424/134.1; 424/192.1; 514/2; 514/8; 514/885; 530/350; 530/387.3; 536/23.1; 536/23.4; 536/23.5; 435/252.3; 435/320.1; 435/471

(58) Field of Search .................... 530/350, 395, 530/388.22, 387.3; 435/70.21, 172.2, 252.3, 320.1, 471; 514/2, 8, 885; 424/134.1, 192.1; 536/23.1, 23.4, 23.5

(56) References Cited

U.S. PATENT DOCUMENTS

| | | |
|---|---|---|
| 4,399,216 A | 8/1983 | Axel |
| 4,683,195 A | 7/1987 | Mullis et al. |
| 4,683,202 A | 7/1987 | Mullis et al. |

FOREIGN PATENT DOCUMENTS

| | | | |
|---|---|---|---|
| EP | 0 440 373 A1 | 1/1991 | |
| WO | 89/029220 | * 4/1989 | .......... C12N/15/00 |
| WO | WO 90/05541 | 5/1990 | |
| WO | WO 92/15671 | 9/1992 | |

OTHER PUBLICATIONS

Basse et al. [Cancer Immunol. Immunother. 34:221–227 (1992)].*
Osband et al., Immunotherapy 11(6):193–195 (1990).*
Linsley et al., J. Exp. Med. 174:561–569 (1991).*
Hird et al., Genes and Cancer (1990) chapter 17.*
Dillman, Ann. Internal Med. 111:592–603 (1989).*
Kahan Cur. Opin Immunol. 4: 553–560(1992).*
Blazar et al. J. Immunol. 157: 3250–3259(1996).*
Perkin et al. J. Neuroimmunol. 65: 31–39 (1996).*
Yi–Qun et al. Int. Immunol. 8: 37–44 (1996).*

Waldmann Science 252: 1657–1662 1991.*
Harris et al TIBTECH 11:42–44 1993.*
Springer et al., "The Lymphocyte Function–Associated LFA–1, CD2, and LFA–3 Molecules: Cell Adhesion Receptors of the Immune System", *A. Rev. Immunol.* 5:223–252 (1987).
Dinarello and Mier, "Medical Intelligence—Current Concepts Lymphokines", *New Engl. Jour. Med.* 317:940–945 (1987).
Weiss et al., "The Role of the T3/Antigen Receptor Complex in T–Cell Activation", *Ann. Rev. Immunol.* 4:593–619 (1986).
McMichael, Ed., "Non–Lineage, LFA–1 Family, and Leucocyte Common Antigens New and Previously Defined Clusters", *Leukocyte Typing III*, Oxford Univ. Press, Oxford, NY (1987) pp. 788–803.
Aruffo and Seed, "Molecular Cloning of a CD28 cDNA by a High–Efficiency COS Cell Expression System", *Proc. Natl. Acad. Sci.* 84:8573–8577 (1987).
Damle et al., "Alloantigen–Specific Cytotoxic and Suppressor T Lymphocytes are Derived from Phenotypically Distinct Precursors", *J. Immunol.* 131: 2296–2300 (1983).
June et al., "T–Cell Proliferation Involving the CD28 Pathway is Associated with Cyclosporine–Resistant Interleukin 2 Gene Expression", *Mol. Cell. Biol.* 7:4472–4481 (1987).
Thompson et al., "CD28 Activation Pathway Regulates the Production of Multiple T–Cell–Derived Lymphokines/Cytokines", *Proc. Natl. Acad. Sci.* 86:1333–1337 (1989).
Lindsten et al., "Regulation of Lymphokine Messenger RNA Stability by a Surface–Mediated T Cell Activation Pathway", *Science* 244:339–343 (1989).
Damle et al., "Monoclonal Antibody Analysis of Human T Lymphocyte Subpopulations Exhibiting Autologous Mixed Lymphocyte Reaction", *Proc. Natl. Acad. Sci.* 78:5096–5098 (1981).
Lesslauer et al., "T90/44 (9.3 Antigen). A Cell Surface Molecule with a Function in Human T Cell Activation", *Eur. J. Immunol.* 16:1289–1296 (1986).

(List continued on next page.)

*Primary Examiner*—Phillip Gambel
(74) *Attorney, Agent, or Firm*—Mandel & Adriano

(57) ABSTRACT

The invention identifies the B7 antigen as a ligand that is reactive with the CD28 receptor on T cells. Fragments and derivatives of the B7 antigen and CD28 receptor, including fusion proteins having amino acid sequences corresponding to the extracellular domains of B7 or CD28 joined to amino acid sequences encoding portions of human immunoglobulin Cγ1, are described. Methods are provided for using B7 antigen, its fragments and derivatives, and the CD28 receptor, its fragments and derivatives, as well as antibodies and other molecules reactive with B7 antigen and/or the CD28 receptor, to regulate CD28 positive T cell responses, and immune responses mediated by T cells. The invention also includes an assay method for detecting ligands reactive with cellular receptors mediating intercellular adhesion.

16 Claims, 19 Drawing Sheets

OTHER PUBLICATIONS

Williams and Barclay, "The Immunoglobulin Superfamily—Domains for Cell Surface Recognition", *Ann. Rev. Immunol.* 6:381–405 (1988).

Shaw and Shimuzu, "Two Molecular Pathways of Human T Cell Adhesion: Establishment of Receptor–Ligand Relationship", *Current Opinion in Immunology*, Eds. Kindt and Long, 1:92–97 (1988).

Moingeon et al., "CD2–Mediated Adhesion Facilitates T Lymphocytes Antigen Recognition Function", *Nature* 339:312–314 (1988).

Makgoba et al., "ICAM–1 A Ligand for LFA–1–Dependent Adhesion of B, T and Myeloid Cells", *Nature* 331:86–88 (1988).

Staunton et al., "Functional Cloning of ICAM–2, A Cell Adhesion Ligand for LFA–1 Homologous to ICAM–1", *Nature* 339:61–64 (1989).

Norment et al., "Cell–Cell Adhesion Mediated by CD8 and MHC Class I Molecules", *Nature* 336:79–81 (1988).

Doyle and Strominger, "Interaction Between CD4 and Class II MHC Molecules Mediates Cell Adhesion", *Nature* 330:256–259 (1987).

Stoolman, "Adhesion Molecules Controlling Lymphocyte Migration", *Cell* 56:907–910 (1989).

Hemler, "Adhesive Protein Receptors on Hematopoietic Cells", *Immunology Today*, 9:109–113 (1988).

Kishimoto et al., "The Leukocyte Integrins", *Adv. Immunol.* 46:149–182 (1989).

Kakiuchi et al., "B Cells as Antigen–Presenting Cells: The Requirement for B Cell Activation", *J. Immunol.* 131:109–114 (1983).

Kreiger et al., "Antigen Presentation by Splenic B Cells: Resting B Cells are Ineffective, Whereas Activated B Cells are Effective Accessory Cells for T Cell Responses", *J. Immunol.* 135:2937–2945 (1985).

McKenzie, "Alloantigen Presentation by B Cells—Requirement for IL–1 and IL–6", *J. Immunol.* 2907–2911 (1988).

Hawrylowicz and Unanue, "Regulation of Antigen–presentation–I—IFN– Induces Antigen–Presenting Properties on B Cells", *J. Immunol.* 141:4083–4088 (1988).

Noelle and Snow, "Cognate Interactions Between Helper T Cells and B Cells", *Immunol. Today* 11:361–368 (1990).

Poo, et al., "Receptor–Directed Focusing of Lymphokine Release by Helper T Cells", *Nature* 332:378–380 (1988).

Bretscher and Cohn, "A Theory of Self–Nonself Discrimination", *Science* 169:1042–1049 (1970).

Janeway, "Approaching the Asymptote? Evolution and Revolution in Immunology", *Cold Spring Harbor Symp. Quant. Biol.* 54:1–14 (1989).

Weiss, "Structure and Function of the T Cell Antigen Receptor", *J. Clin. Invest.* 86:1015–1022 (1990).

Allen, "Antigen Processing at the Molecular Level", *Immunol. Today* 8:270–273 (1987).

Schwartz, "A Cell Culture Model for T Lymphocyte Clonal Anergy", *Science* 248:1349–1356 (1990).

Weaver and Unanue, "The Costimulatory Function of Antigen–Presenting Cells", *Immunol. Today* 11:49–55 (1990).

Springer, "Adhesion Receptors of the Immune System", *Nature* 346:425–434 (1990).

Freeman et al. "B7, A New Member of the Ig Superfamily with Unique Expression on Activated and Neoplastic B Cells", *J. Immunol.* 143(8):2714–2722 (1989).

Freedman et al., "B7, A B Cell–Restricted Antigen That Identifies Preactivated B Cells" *J. Immunol.* 139:3260–3267 (1987).

Clark et al., "Polypeptides on Human B Lymphocytes Associated with Cell Activation", *Human Immunology* 16:100–113 (1986).

Yokochi et al., "B Lymphoblast Antigen (BB–1) Expressed on Epstein–Barr Virus–Activated B Cell Blasts, B Lymphoblastoid Cell Lines, and Burkitt's Lymphomas", *J. Immunol.* 128:823–827 (1981).

Capon et al., "Designing CD4 Immunoadhesins for AIDS Therapy" *Nature* 337:525–531 (1989).

Damle, "Differential Regulatory Signals Delivered by Antibody Binding to the CD28 (Tp44) Molecule During the Activation of Human T Lymphocytes", *J. Immunol.* 140:1753–1761 (1988).

Ledbetter et al., "CD28 Ligation to T–Cell Activation: Evidence for Two Signal Transduction Pathways" *Blood* 75(7):1531–1539 (1990).

Rosenberg et al., "A New Approach to the Adoptive Immunotherapy of Cancer with Tumor–Infiltrating Lymphocytes", *Science* 223:1318–1321 (1986).

Havell, "Evidence that Tumor Necrosis Factor has an Important Role in Antibacterial Resistance", *J. Immunol.* 143:2894–2399 (1990).

Koff and Fann, "Human Tumor Necrosis Factor–Alpha Kills Herpesvirus–Infected But not Normal Cells", *Lymphokine Res.* 5:215–221 (1986).

Goldstein and Laszio: "The Role of Interferon Cancer Therapy—A Current Perspective", *CA: A Cancer Journal for Clinicians*, 38:258–277 (1988).

Storb et al., "Marrow Transplantaton for Severe Aplastic Anemia: Methotrexate Alone Compared with a Combination of Methotrexate and Cyclosporine for Prevention of Acute Graft–Versus–Host Disease," *Blood*, 68:119–125 (1986).

Storb and Thomas, "Graft–versus–Host Disease in Dog and Man: The Seattle Experience", *Immunol. Rev.* 88:215–238 (1985).

Brandt et al., "Effect of Recombinant Human Granulocyte–Macrophage Colony–Stimulating Factor on Hematopoietic Reconstitution After High–Dose Chemotherapy and Autologous Bone Marrow Transplantation", *N. Eng. J. Med.* 318:869–876 (1988).

Groopman et al., "Effect of Recombinant Human Granulocyte–Macrophage Colony–Stimulating Factor on Myelopoiesis in the Acquired Immunodeficiency Syndrome", *N. Eng. Med.* 317:593–626 (1987).

Vadan–Raj et al., "Effects of Recombinant Human Granulocyte–Macrophage Colony=Stimulating Factor in Patients with Myelodysplastic Syndromes", *N. Eng. J. Med.* 317:1545–1551 (1987).

Mulligan and Berg, "Expression of a Bacterial Gene in Mammalian Cells", *Science* 209:1422–1427 (1988).

Urlaub and Chasin, "Isolation of Chinese Hamster Cell Mutants Deficient in Dihydrofolate Reductase Activity", *Proc. Natl. Acad. Sci.* 77:4616–4220 (1980).

Ledbetter and Herzenberg, "Xenogeneic Monoclonal Antibodies to Mouse Lymphoid Differentiation Antigens", *Immunol. Rev.* 47:62–90 (1979).

Hansen et al., "Monoclonal Antibodies Identifying a Novel T–Cell Antigen and Ia Antigens of Human Lymphocytes", *Immunogenetics* 10:247–260 (1980).

Parham, "On the Fragmentation of Monoclonal IgG1, IgG2, and IgG2b from BALB/c Mice", *J. Immunol.* 131:2895–2902 (1983).

Kuritani and Cooper, "Human B Cell Differentiation", *J. Exp. Med.* 155:839–848 (1982).

Gilliland et al., "Signal Transduction in Lymphocyte Activation Through Crosslinking of HLA Class I Molecules", *Human Immunology* 25:269–289 (1989).

Wayner et al., "Identification and Characterization of the T Lymphocyte Adhesion Receptor for an Alternative Cell Attachment Domain (CS–1) in Plasma Fibronectin", *J. Cell. Biol.* 109:1321–1330 (1989).

Goding in Monoclonal Antibodies: Principles and Practices, Academic Press, Orlando, FL pp. 118–125 (1983).

Hellstrom et al., "Monoclonal Antibodies in Two Determinants of Melanoma–Antigen p97 Act Synergistically in Complement–Dependent Cytotoxicity", *J. Immunol.* 127:157–160 (1981).

Graham and Van Der Eb, "A New Technique for the Assay of Infectivity of Human Adenovirus 5 DNA", *Virology* 52:456–467 (1973).

Malik et al., "Molecular Cloning, Sequence Analysis, and Functional Expression of a Novel Growth Regulator, Oncostatin M", *Molecular and Cellular Biology* 9:2847–2853 (1989).

Linsley et al.,"Elevated Levels of a High Molecular Weight Antigen Detected by Antibody W1 in Sera from Breast Cancer Patients", *Cancer Res.* 46:5444–5450 (1986).

Hellstrom et al., "Monoclonal Mouse Antibodies Raised Against Human Lung Carcinoma", *Cancer Res.* 46:3917–3923 (1986).

Gladstone and Pious, "Stable Variants Affecting B Cell Alloantigens in Human Lymphoid Cells", *Nature* 271:459–461 (1978).

Beatty et al., "Absence of Monoclonal–Antibody–Defined Protein Complex in Boy with Abnormal Leucocyte Function", *Lancet* 1:535–537 (1984).

Gaur et al., "Conservation of HLA Class I Private Epitopes in Macaques", *Immunogenetics* 27:356–361 (1988).

Pohlman et al., "An Endothelial Cell Surface Factor(s) Induced in Vitro by Lipopolysaccharide, Interleukin 1, and Tumor Necrosis Factor–α Increases Neutrophil Adherence by A CDw18–Dependent Mechanism", *J. Immunol.* 136:4548–4553 (1986).

Kozbor et al., "Tp44 Molecules Involved in Antigen–Independent T Cell Activation are Expressed on Human Plasma Cells", *J. Immunol.* 138:4128–4132 (1987).

Chiorazzi et al., "Induction of Human Antibody Responses In Vitro with Emphasis on Allogeneic Helper Factors", *Immunol. Rev.* 45:219–241 (1979).

Ledbetter et al., "Antibodies to Tp67 and Tp44 Augment and Sustain Proliferative Responses of Activated T Cells", *J. Immunol.* 135:2331–2336 (1985).

Martin et al., "A 44 Kilodalton Cell Surface Homodimer Regulates Interleukin 2 Production by Activated Human T Lymphocytes", *J. Immunol.* 136:3282–3287 (1986).

Damle and Doyle, "Stimulation Via the Cd3 and CD28 Molecules Induces Responsiveness to IL–4 in $CD4^+CD29^+CD45R^-$ Memory T Lymphocytes", *J. Immunol.* 143:1761–1767 (1989).

Damle et al., "Immunoregulatory T Lymphocytes in Man", *J. Immunol.* 139:1501–1508 (1987).

Damle et al., "Activation of Antigen–specific Suppressor T Lymphocytes in Man Involves Dual Recognition of Self Class I MHC Molecules and LEU–4/T3–Associated Structures on the Surface of Inducer T Lymphocytes", *J. Immunol.* 133;1235–1240 (1984).

Aruffo et al., "CD44 is the Principal Cell Surface Receptor for Hyaluronate", *Cell* 61:1303–1313 (1990).

Seed and Aruffo, "Molecular Closing of the CD2 Antigen, the T–Cell Erythrocyte Receptor, by a Rapid Immunoselection Procedure", *Proc. Natl. Acad. Sci.* 84: 3365–3369 (1987).

Linsley et al., "Biosynthesis of High Molecular Weight Breast Carcinoma Associated Mucin Glycoproteins", *J. Biol. Chem.* 263:8390–8397 (1988).

Chomczynki and Sacchi, "Single–Step Method of RNA Isolation by Acid Guanidinium Thiocyanate–Phenol–Chloroform Extraction", *Anal. Biochem.* 162:156–159 (1987).

Alzari et al. "Three–Dimensional Structure of Antibodies", *Annu. Rev. Immunol.* 6:555–580 (1980).

Schneck et al., "Inhibition of an Allospecific T Cell Hybridoma by Soluble Class I Proteins and Peptides: Estimation of the Affinity of a T Cell Receptor for MHC", *Cell* 56:47–55 (1989).

Recny et al., "Structural and Functional Characterization of the CD2 Immunoadhesion Domain", *J. Biol. Chem.* 265:8542–8549 (1990).

Clayton et al., "Identification of Human CD4 Residues Affecting Class II MHC Versus HIV–1 gp120 Binding", *Nature* 339:548–551 (1989).

Lasky et al., "Delineation of a Region of the Human Immunodeficiency Virus Type 1 gp120 Glycoprotein Critical for Interaction with the CD4 Receptor", *Cell* 50:975–985 (1987).

Linsley et al., "T–Cell Antigen CD28 Mediates Adhesion with B Cells by Interacting with Activation Antigen B7/BB–1", *Proc. Natl. Acad. Sci.* 87:5031–5035 (1990).

Damle et al., "Direct helper T cell–induced B cell differentiation involves interaction between T cell antigen CD28 and B cell activation antigen B7", *Eur. J. Immunol.*, 21:1227–1282, (1991).

Linsley, et al., "Binding of the B Cell Activation Antigen B7 to CD28 Costimulates T Cell Proliferation and Interleukin 2 mRNA Accumulation", *J. Exp. Med*, 173:721–730, (1991).

\* cited by examiner

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 39 base pairs
      (B) TYPE: nucleic acid (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:1:

CTAGCCACTG AAGCTTCACC ATGGGTGTAC TGCTCACAC                39

(2) INFORMATION FOR SEQ ID NO:2:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:2:

TGGCATGGGC TCCTGATCAG GCTTAGAAGG TCCGGGAAA                39

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:3:

TTTGGGCTCC TGATCAGGAA AATGCTCTTG CTTGGTTGT                39

(2) INFORMATION FOR SEQ ID NO:4:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens

```
     (xi) SEQUENCE DESCRIPTION: SEQ ID NO:4:

AAGCAAGAGC ATTTTCCTGA TCAGGAGCCC AAATCTTCTG ACAAAACTCA CACATCCCCA      60

CCGTCCCCAG CACCTGAACT CCTG                                            84

(2) INFORMATION FOR SEQ ID NO:5:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Homo sapiens (xi) SEQUENCE DESCRIPTION: SEQ ID NO:5:

CTTCGACCAG TCTAGAAGCA TCCTCGTGCG ACCGCGAGAG C                         41

(2) INFORMATION FOR SEQ ID NO:6:

(i) SEQUENCE CHARACTERISTICS:
          (A) LENGTH: 47 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Homo sapiens (xi) SEQUENCE DESCRIPTION: SEQ ID NO:6:

CATTGCACAG TCAAGCTTCC ATGCCCATGG GTTCTCTGGC CACCTTG                   47

(2) INFORMATION FOR SEQ ID NO:7:

(i) SEQUENCE CHARACTERISTICS:
          (A) LENGTH: 39 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Homo sapiens (xi) SEQUENCE DESCRIPTION: SEQ ID NO:7:

ATCCACAGTG CAGTGATCAT TTGGATCCTG GCATGTGAC                            39
```

METHOD OF REGULATING CELLULAR PROCESSES MEDIATED BY B7 AND CD28

This application is a file wrapper continuation application of U.S. Ser. No. 07/722,101, filed Jun. 27, 1991, now abandoned which is a continuation-in-part of U.S. Ser. No. 07/547,980, filed Jul. 2, 1990, now abandoned, which was a continuation-in-part of U.S. Ser. No. 07/498,949, filed Mar. 26, 1990, now abandoned.

FIELD OF THE INVENTION

The present invention relates to the identification of an interaction between the CD28 receptor and its ligand, the B7 antigen, and to a method for regulating cellular interactions using the antigen, fragments and derivatives thereof.

BACKGROUND OF THE INVENTION

The generation of a T lymphocyte ("T cell") immune response is a complex process involving cell-cell interactions (Springer et al., *A. Rev. Immunol.* 5:223–252 (1987)), particularly between T and B cells, and production of soluble immune mediators (cytokines or lymphokines) (Dinarello and Mier, *New Engl. Jour. Med.* 317:940–945 (1987)). This response is regulated by several T-cell surface receptors, including the T-cell receptor complex (Weiss et al., *Ann. Rev. Immunol.* 4:593–619 (1986)) and other "accessory" surface molecules (Springer et al., (1987) supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y. (1987)).

One such accessory molecule is the CD28 antigen, a homodimeric glycoprotein of the immunoglobulin superfamily (Aruffo and Seed, *Proc. Natl. Acad. Sci.* 84:8573–8577 (1987)) found on most mature human T cells (Damle et al., *J. Immunol.* 131:2296–2300 (1983)). Current evidence suggests that this molecule functions in an alternative T cell activation pathway distinct from that initiated by the T-cell receptor complex (June et al., *Mol. Cell. Biol.* 7:4472–4481 (1987)). Monoclonal antibodies (mAbs) reactive with CD28 antigen can augment T cell responses initiated by various polyclonal stimuli (reviewed by June et al., supra). These stimulatory effects may result from mAb-induced cytokine production (Thompson et al., *Proc. Natl. Acad. Sci* 86:1333–1337 (1989); Lindsten et al., *Science* 244:339–343 (1989)) as a consequence of increased mRNA stabilization (Lindsten et al., (1989), supra). Anti-CD28 mAbs can also have inhibitory effects, i.e., they can block autologous mixed lymphocyte reactions (Damle et al., *Proc. Natl. Acad. Sci.* 78:5096–6001 (1981)) and activation of antigen-specific T cell clones (Lesslauer et al., *Eur. J. Immunol.* 16:1289–1296 (1986)).

The in vivo function of CD28 antigen is not known, although its structure (Aruffo and Seed, (1987), supra) suggests that like other members of the immunoglobulin superfamily (Williams and Barclay, *Ann. Rev. Immunol.* 6:381–405 (1988)), it might function as a receptor. CD28 antigen could conceivably function as a cytokine receptor, although this seems unlikely since it shares no homology with other lymphokine or cytokine receptors (Aruffo and Seed, (1987) supra).

Alternatively, CD28 might be a receptor which mediates cell-cell contact ("intercellular adhesion"). Antigen-independent intercellular interactions involving lymphocyte accessory molecules are essential for an immune response (Springer et al., (1987), supra). For example, binding of the T cell-associated protein, CD2, to its ligand LFA-3, a widely expressed glycoprotein (reviewed in Shaw and Shimuzu, *Current Opinion in Immunology*, Eds. Kindt and Long, 1:92–97 (1988)), is important for optimizing antigen-specific T cell activation (Moingeon et al., *Nature* 339:314 (1988)). Another important adhesion system involves binding of the LFA-1 glycoprotein found on lymphocytes, macrophages, and granulocytes (Springer et al., (1987), supra; Shaw and Shimuzu (1988), supra) to its ligands ICAM-1 (Makgoba et al., *Nature* 331:86–88 (1988)) and ICAM-2 (Staunton et al., *Nature* 339:61–64 (1989)). The T cell accessory molecules CD8 and CD4 strengthen T cell adhesion by interaction with MHC class I (Norment et al., *Nature* 336:79–81 (1988)) and class II (Doyle and Strominger, *Nature* 330:256–259 (1987)) molecules, respectively. "Homing receptors" are important for control of lymphocyte migration (Stoolman, *Cell* 56:907–910 (1989)). The VLA glycoproteins are integrins which appear to mediate lymphocyte functions requiring adhesion to extracellular matrix components (Hemler, *Immunology Today* 9:109–113 (1988)). The CD2/LFA-3, LFA-1/ICAM-1 and ICAM-2, and VLA adhesion systems are distributed on a wide variety of cell types (Springer et al., (1987), supra; Shaw and Shimuzu, (1988,) supra and Hemler, (1988), supra).

Intercellular adhesion interactions mediated by integrins are strong interactions that may mask other intercellular adhesion interactions. For example, interactions mediated by integrins require divalent cations (Kishimoto et al., *Adv. Immunol.* 46:149–182 (1989). These interactions may mask other intercellular adhesion interactions that are divalent cation independent. Therefore, it would be useful to develop assays that permit identification of non-integrin mediated ligand/receptor interactions.

T cell interactions with other cells such as B cells are essential to the immune response. Levels of many cohesive molecules found on T cells and B cells increase during an immune response (Springer et al., (1987), supra; Shaw and Shimuzu, (1988), supra; Hemler (1988), supra). Increased levels of these molecules may help explain why activated B cells are more effective at stimulating antigen-specific T cell proliferation than are resting B cells (Kaiuchi et al., *J. Immunol.* 131:109–114 (1983); Kreiger et al., *J. Immunol* 135:2937–2945 (1985); McKenzie, *J. Immunol.* 141: 2907–2911 (1988); and Hawrylowicz and Unanue, *J. Immunol.* 141:4083–4088 (1988)). The fact that anti-CD28 mAbs inhibit mixed lymphocyte reactions (MLR) may suggest that the CD28 antigen is also an adhesion molecule.

Optimal activation of B lymphocytes and their subsequent differentiation into immunoglobulin secreting cells is dependent on the helper effects of major histocompatibility complex (MHC) class II antigen (Ag)-reactive CD4 positive T helper (CD4$^+$ T$_h$) cells and is mediated via both direct (cognate) T$_h$-B cell intercellular contact-mediated interactions and the elaboration of antigen-nonspecific cytokines (non-cognate activation; see, e.g. Noel and Snow, *Immunol. Today* 11:361 (1990)). Although T$_h$-derived cytokines can stimulate B cells (Moller, *Immunol. Rev.* 99:1 (1987)), their synthesis and directional exocytosis is initiated and sustained via cognate interactions between antigen-primed T$_h$ cells and antigen-presenting B cells (Moller, supra). The successful outcome of T$_h$-B interactions requires participation of transmembrane receptor-ligand pairs of co-stimulatory accessory/adhesion molecules on the surface of T$_h$ and B cells which include CD2 (LFA-2); CD58 (LFA-3), CD4:MHC class II, CD11a/CD18 (LFA-1):CD54 (1CAM-1).

During cognate $T_h$:B interaction, although both $T_h$ and B cells cross-stimulate each other, their functional differentiation is critically dependent on the provision by $T_h$ cells of growth and differentiation-inducing cytokines such as IL-2, IL-4 and IL-6 (Noel, supra, Kupfer et al., supra, Brian, supra and Moller, supra). Studies by Poo et al. (*Nature* 332:378 (1988)) on cloned $T_h$:B interaction indicate that interaction of the T cell receptor complex (TcR) with nominal Ag-MHC class II on B cells results in focused release of $T_h$ cell-derived cytokines in the area of $T_h$ and B cell contact (vectorially oriented exocytosis). This may ensure the activation of only B cells presenting antigen to $T_h$ cells, and also avoids activation of bystander B cells.

It was proposed many years ago that B lymphocyte activation requires two signals (Bretscher and Cohn, *Science* 169:1042–1049 (1970)) and now it is believed that all lymphocytes require two signals for their optimal activation, an antigen specific or clonal signal, as well as a second, antigen non-specific signal (Janeway, supra). The signals required for a T helper cell ($T_h$) antigenic response are provided by antigen-presenting cells (APC). The first signal is initiated by interaction of the T cell receptor complex (Weiss, *J. Clin. Invest.* 86:1015 (1990)) with antigen presented in the context of class II major histocompatibility complex (MHC) molecules on the APC (Allen, *Immunol. Today* 8:270 (1987)). This antigen-specific signal is not sufficient to generate a full response, and in the absence of a second signal may actually lead to clonal inactivation or anergy (Schwartz, *Science* 248:1349 (1990)). The requirement for a second "costimulatory" signal provided by the MHC has been demonstrated in a number of experimental systems (Schwartz, supra; Weaver and Unanue, *Immunol. Today* 11:49 (1990)). The molecular nature of these second signal(s) is not completely understood, although it is clear in some cases that both soluble molecules such as interleukin (IL)-1 (Weaver and Unanue, supra) and membrane receptors involved in intercellular adhesion (Springer, *Nature* 346:425 (1990)) can provide costimulatory signals.

Freeman et al. (*J. Immunol.* 143(8):2714–2722 (1989)) isolated and sequenced a cDNA clone encoding a B cell activation antigen recognized by mAb B7 (Freeman et al., *J. Immunol.* 138:3260 (1987)). COS cells transfected with this cDNA have been shown to stain by both labeled mAb B7 and mAb BB-1 (Clark et al., *Human Immunol.* 16:100–113 (1986); Yokochi et al., *J. Immunol.* 128:823 (1982)); Freeman et al., (1989) supra; and Freedman et al., (1987), supra)). Expression of the B cell activation antigen has been detected on cells of other lineages. For example, studies by Freeman et al. (1989) have shown that monocytes express low levels of mRNA for B7.

Expression of soluble derivatives of cell-surface glycoproteins in the immunoglobulin gene superfamily has been achieved for CD4, the receptor for HIV-1, using hybrid fusion molecules consisting of DNA sequences encoding portions of the extracellular domain of CD4 receptor fused to antibody domains (human immunoglobulin C gamma 1), as described by Capon et al., *Nature* 337:525–531 (1989).

While the CD28 antigen has functional and structural characteristics of a receptor, until now, a natural ligand for this molecule has not been identified. It would be useful to identify ligands that bind with the CD28 antigen and other receptors and to use such ligand(s) to regulate cellular responses, such as T cell and B cell interactions, for use in treating pathological conditions.

SUMMARY OF THE INVENTION

Accordingly, the present invention identifies the B7 antigen as a ligand recognized by the CD28 receptor. The B7 antigen, or its fragments or derivatives are reacted with CD28 positive T cells to regulate T cell interactions with other cells. Alternatively, the CD28 receptor, its fragments or derivatives are reacted with B7 antigen to regulate interactions of B7 positive cells with T cells. In addition, antibodies or other molecules reactive with the B7 antigen or CD28 receptor may be used to inhibit interaction of cells associated with these molecules, thereby regulating T cell responses.

A preferred embodiment of the invention provides a method for regulating CD28 specific T cell interactions by reacting CD28 positive T cells with B7 antigen, or its fragments or derivatives, so as to block the functional interaction of T cells with other cells. The method for reacting a ligand for CD28 with T cells may additionally include the use of anti-CD monoclonal antibodies such as anti-CD2 and/or anti-CD3 monoclonal antibody.

In an alternative embodiment, the invention provides a method for regulating immune responses by contacting CD28 positive T cells with fragments containing at least a portion of the DNA sequence encoding the amino acid sequence corresponding to the extracellular domain of B7 antigen. In addition, derivatives of B7 antigen may be used to regulate immune responses, wherein the derivatives are fusion protein constructs including at least a portion of the extracellular domain of B7 antigen and another protein, such as human immunoglobulin C gamma 1, that alters the solubility, binding affinity and/or valency of B7 antigen. For example, in a preferred embodiment, DNA encoding amino acid residues from about position 1 to about position 215 of the sequence corresponding to the extracellular domain of B7 antigen is joined to DNA encoding amino acid residues of the sequences corresponding to the hinge, CH2 and CH3 regions of human Ig Cγ1 to form a DNA fusion product which encodes B7Ig fusion protein.

In another preferred embodiment, DNA encoding amino acid residues from about position 1 to about position 134 of the sequence corresponding to the extracellular domain of the CD28 receptor is joined to DNA encoding amino acid residues of the sequences corresponding to the hinge, CH2 and CH3 regions of human Ig Cγ1 to form a CD28Ig fusion protein.

Alternatively, fragments or derivatives of the CD28 receptor may be reacted with B cells to bind the B7 antigen and regulate T cell/B cell interactions. The methods for regulating T cell interactions may be further supplemented with the addition of a cytokine.

In another embodiment, the invention provides a method for treating immune system diseases mediated by T cell by administering B7 antigen, including B7Ig fusion protein, to react with T cells by binding the CD28 receptor.

In yet another embodiment, a method for inhibiting T cell proliferation in graft versus host disease is provided wherein CD28 positive T cells are reacted with B7 antigen, for example in the form of the B7Ig fusion protein, to bind to the CD28 receptor, and an immunosuppressant is administered.

The invention also provides a cell adhesion assay to identify ligands that interact with target receptors that mediate intercellular adhesion, particularly adhesion that is divalent cation independent.

DETAILED DESCRIPTION OF THE INVENTION

Figure 1:
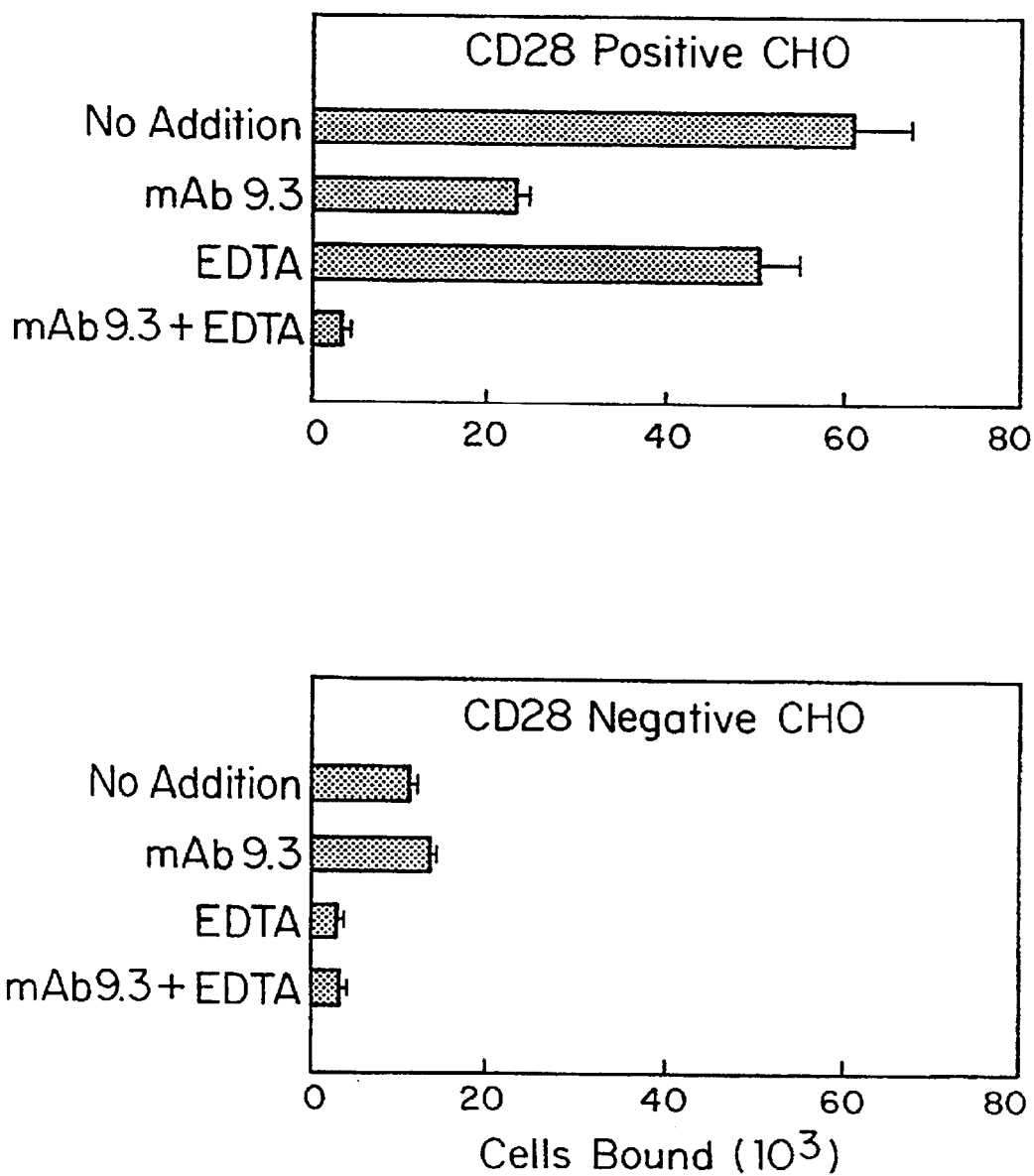
FIG. 1 are bar graphs showing the results of cellular adhesion experiments using CD28 positive (CD28$^+$) and CD28 negative (CD28$^-$) CHO cells as described in Example 1, infra.

In order that the invention herein described may be more fully understood, the following description is set forth.

This invention is directed to the identification of a ligand reactive with CD28 antigen (hereafter referred to as "CD28 receptor"), and to methods of using the ligand and its fragments and derivatives, including fusion proteins. Also disclosed is a cell adhesion assay method to detect ligands for cell surface receptors.

Recently, Freeman et al., (*J. Immunol.* 143(8):2714–2722 (1989)) isolated and sequenced a cDNA clone encoding a B cell activation antigen recognized by monoclonal antibody (mAb) B7 (Freedman et al., *J. Immunol.* 139:3260 (1987)). COS cells transfected with this cDNA were shown to stain by both mAb B7 and mAb BB-1 (Clark et al., *Human Immunology* 16:100–113 (1986), and Yokochi et al., (1981), supra; Freeman et al., (1989) supra; and Freedman et al., (1987), supra)). The ligand for CD28 was identified by the experiments described herein, as the B7/BB-1 antigen isolated by Freeman et al., (Freedman et al., and Freeman et al., supra, both of which are incorporated by reference herein).

For convenience, the ligand for CD28, identified as the B7/BB-1 antigen, is referred to herein as the "B7 antigen".

The term "fragment" as used herein means a portion of the amino acid sequence corresponding to the B7 antigen or CD28 receptor. For example, a fragment of the B7 antigen useful in the method of the present invention is a polypeptide containing a portion of the amino acid sequence corresponding to the extracellular portion of the B7 antigen, i.e. the DNA encoding amino acid residues from position 1 to 215 of the sequence corresponding to the B7 antigen described by Freeman et al., supra. A fragment of the CD28 antigen that may be used is a polypeptide containing amino acid residues from about position 1 to about position 134 of the sequence corresponding to the CD28 receptor as described by Aruffo and Seed, *Proc. Natl. Acad. Sci. (USA)* 84:8573–8577 (1987).

The term "derivative" as used herein includes a fusion protein consisting of a polypeptide including portions of the amino acid sequence corresponding to the B7 antigen or CD28 antigen. For example, a derivative of the B7 antigen useful in the method of the present invention is a B7Ig fusion protein that comprises a polypeptide corresponding to the extracellular domain of the B7 antigen and an immunoglobulin constant region that alters the solubility, affinity and/or valency (valency is defined herein as the number of binding sites available per molecule) of the B7 antigen.

The term "derivative" also includes monoclonal antibodies reactive with the B7 antigen or CD28 receptor, or fragments thereof, and antibodies reactive with the B7Ig and CD28Ig fusion proteins of the invention.

The B7 antigen and/or its fragments or derivatives for use in the present invention may be produced in recombinant form using known molecular biology techniques based on the cDNA sequence published by Freeman et al., supra. Specifically, cDNA sequences encoding the amino acid sequence corresponding to the B7 antigen or fragments or derivatives thereof can be synthesized by the polymerase chain reaction (see U.S. Pat. No. 4,683,202) using primers derived from the published sequence of the antigen (Freeman et al.,supra). These cDNA sequences can then be assembled into a eukaryotic or prokaryotic expression vector and the resulting vector can be used to direct the synthesis of the ligand for CD28 by appropriate host cells, for example COS or CHO cells. CD28 receptor and/or its fragments or derivatives may also be produced using recombinant methods.

In a preferred embodiment, DNA encoding the amino acid sequence corresponding to the extracellular domain of the B7 antigen, containing amino acids from about position 1 to about position 215, is joined to DNA encoding the amino acid sequences corresponding to the hinge, CH2 and CH3 regions of human Ig Cγ1, using PCR, to form a construct that is expressed as B7Ig fusion protein. DNA encoding the amino acid sequence corresponding to the B7Ig fusion protein has been deposited with the American Type Culture Collection (ATCC), 10801 University Boulevard, Manassas, Va. 20110-2209, under the Budapest Treaty on May 31, 1991 and accorded accession number 68627.

In another embodiment, DNA encoding the amino acid sequence corresponding to the extracellular domain of the CD28 receptor, containing amino acids from about position 1 to about position 134, is joined to DNA encoding the amino acid sequences corresponding to the hinge, CH2 and CH3 regions of human Ig Cγ1 using PCR to form a construct expressed as CD28Ig fusion protein. DNA encoding the amino acid sequence corresponding to the CD28Ig fusion protein has been deposited in the ATCC, 10801 University Boulevard, Manassas, Va. 20110-2209 under the Budapest Treaty on May 31, 1991 and accorded accession number 68628.

The techniques for assembling and expressing DNA encoding the amino acid sequences corresponding to B7 antigen and soluble B7Ig and CD28Ig fusion proteins, e.g synthesis of oligonucleotides, PCR, transforming cells, constructing vectors, expression systems, and the like are well-established in the art, and most practitioners are familiar with the standard resource materials for specific conditions and procedures. However, the following paragraphs are provided for convenience and notation of modifications where necessary, and may serve as a guideline.

Cloning and Expression of Coding Sequences for Receptors and Fusion Proteins cDNA clones containing DNA encoding CD28 and B7 proteins are obtained to provide DNA for assembling CD28 and B7 fusion proteins as described by Aruffo and Seed, *Proc. Natl. Acad. Sci. USA* 84:8573–8579 (1987) (for CD28); and Freeman et al., *J. Immunol.* 143:2714–2722 (1989) (for B7), incorporated by reference herein. Alternatively, cDNA clones may be prepared from RNA obtained from cells expressing B7 antigen and CD28 receptor based on knowledge of the published sequences for these proteins (Aruffo and Seed, and Freeman, supra) using standard procedures.

The cDNA is amplified using the polymerase chain reaction ("PCR") technique (see U.S. Pat. Nos. 4,683,195 and 4,683,202 to Mullis et al. and Mullis & Faloona, *Methods Enzymol.* 154:335–350 (1987)) using synthetic oligonucleotides encoding the sequences corresponding to the extracellular domain of the CD28 and B7 proteins as primers. PCR is then used to adapt the fragments for ligation to the DNA encoding amino acid fragments corresponding to the human immunoglobulin constant γ1 region, i.e. sequences encoding the hinge, CH2 and CH3 regions of Ig Cγ1 to form B7Ig and CD28Ig fusion constructs and to expression plasmid DNA to form cloning and expression plasmids containing sequences corresponding to B7 or CD28 fusion proteins.

To produce large quantities of cloned DNA, vectors containing DNA encoding the amino acid sequences corresponding to the fusion constructs of the invention are transformed into suitable host cells, such as the bacterial cell line MC1061/p3 using standard procedures, and colonies are screened for the appropriate plasmids.

The clones obtained as described above are then transfected into suitable host cells for expression. Depending on the host cell used, transfection is performed using standard techniques appropriate to such cells. For example, transfection into mammalian cells is accomplished using DEAE-dextran mediated transfection, $CaPO_4$ co-precipitation, lipofection, electroporation, or protoplast fusion, and other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression plasmids containing cDNAs encoding sequences corresponding to CD28 and B7 for cloning and expression of CD28Ig and B7Ig fusion proteins include the OMCD28 and OMB7 vectors modified from vectors described by Aruffo and Seed, *Proc. Natl. Acad. Sci. USA* (1987), supra, (CD28); and Freeman et al., (1989), supra, (B7), both of which are incorporated by reference herein. Preferred host cells for expression of CD28Ig and B7Ig proteins include COS and CHO cells.

Expression in eukaryotic host cell cultures derived from multicellular organisms is preferred (see *Tissue Cultures*, Academic Press, Cruz and Patterson, Eds. (1973)). These systems have the additional advantage of the ability to splice out introns and thus can be used directly to express genomic fragments. Useful host cell lines include Chinese hamster ovary (CHO), monkey kidney (COS), VERO and HeLa cells. In the present invention, cell lines stably expressing the fusion constructs are preferred.

Expression vectors for such cells ordinarily include promoters and control sequences compatible with mammalian cells such as, for example, CMV promoter (CDM8 vector) and avian sarcoma virus (ASV) (πLN vector). Other commonly used early and late promoters include those from Simian Virus 40 (SV 40) (Fiers, et al., *Nature* 273:113 (1973)), or other viral promoters such as those derived from polyoma, Adenovirus 2, and bovine papilloma virus. The controllable promoter, hMTII (Karin, et al., *Nature* 299:797–802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eukaryotes.

Although preferred host cells for expression of the DNA constructs include eukaryotic cells such as COS or CHO cells, other eukaryotic microbes may be used as hosts. Laboratory strains of *Saccharomyces cerevisiae*, Baker's yeast, are most used although other strains such as *Schizosaccharomyces pombe* may be used. Vectors employing, for example, the 2μ origin of replication of Broach, *Meth. Enz.* 101:307 (1983), or other yeast compatible origins of replications (see, for example, Stinchcomb et al., *Nature* 282:39 (1979)); Tschempe et al., *Gene* 10:157 (1980); and Clarke et al., *Meth. Enz.* 101:300 (1983)) may be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the CMV promoter provided in the CDM8 vector (Toyama and Okayama, *FEBS* 268:217–221 (1990); the promoter for 3-phosphoglycerate kinase (Hitzeman et al., *J.*

*Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., *Nature* 198: 1056 (1977)), the tryptophan (trp) promoter system (Goeddel et al., *Nucleic Acids Res.* 8:4057 (1980)) and the lambda derived $P_L$ promoter and N-gene ribosome binding site (Shimatake et al., *Nature* 292:128 (1981)).

The nucleotide sequences encoding the amino acid sequences corresponding to the CD28Ig and B7Ig fusion proteins, may be expressed in a variety of systems as set forth below. The cDNA may be excised by suitable restriction enzymes and ligated into suitable prokaryotic or eukaryotic expression vectors for such expression. Because CD28 receptors occur in nature as dimers, it is believed that successful expression of these proteins requires an expression system which permits these proteins to form as dimers. Truncated versions of these proteins (i.e. formed by introduction of a stop codon into the sequence at a position upstream of the transmembrane region of the protein) appear not to be expressed. The expression of CD28 antigen in the form of a fusion protein permits dimer formation of the protein. Thus, expression of CD28 antigen as a fusion product is preferred in the present invention.

Sequences of the resulting fusion protein constructs are confirmed by DNA sequencing using known procedures, for example as described by Sanger et al., *Proc. Natl. Acad. Sci. USA* 74:5463 (1977) as further described by Messing et al., *Nucleic Acids Res.* 9:309 (1981) or by the method of Maxam et al. *Methods Enzymol.* 65:499 (1980)).

Recovery of Protein Products

As noted above, the CD28 receptor is not readily expressed as a mature protein using direct expression of DNA encoding the amino acid sequence corresponding to the truncated protein. To enable homodimer formation, it is preferred that DNA encoding the amino acid sequence corresponding to the extracellular domain of CD28 and including the codons for a signal sequence such as oncostatin M in cells capable of appropriate processing, is fused with DNA encoding amino acids corresponding to the Fc domain of a naturally dimeric protein. Purification of the fusion protein products after secretion from the cells is thus facilitated using antibodies reactive with the anti-immunoglobulin portion of the fusion proteins. When secreted into the medium, the fusion protein product is recovered using standard protein purification techniques, for example by application to protein A columns.

In addition to the fusion proteins of the invention, monoclonal antibodies reactive with the B7 antigen and CD28 receptor, and reactive with B7Ig and CD28Ig fusion proteins, may be produced by hybridomas prepared using known procedures, such as those introduced by Kohler and Milstein (see Kohler and Milstein, *Nature,* 256:495–97 (1975), and modifications thereof, to regulate cellular interactions.

These techniques involve the use of an animal which is primed to produce a particular antibody. The animal can be primed by injection of an immunogen (e.g. the B7Ig fusion protein) to elicit the desired immune response, i.e. production of antibodies reactive with the ligand for CD28, the B7 antigen, from the primed animal. A primed animal is also one which is expressing a disease. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the B7Ig fusion protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (see Zola et al., in *Monoclonal Hybridoma Antibodies: Techniques and Applications,* Hurell (ed.) pp. 51–52 (CRC Press, 1982)). Hybridomas produced according to these methods can be propagated in vitro or in vivo (in ascites fluid) using techniques known in the art (see generally Fink et al., *Prog. Clin. Pathol.,* 9:121–33 (1984), FIG. 6–1 at p. 123).

Generally, the individual cell line may be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region of the extracellular domain of B7 or CD28 antigen, such as Fab, $F(ab')_2$ and Fv fragments, may be produced. Such fragments can be produced using techniques well established in the art (see e.g. Rousseaux et al., in *Methods Enzymol.,* 121:663–69, Academic Press (1986)).

Uses

General

The experiments described below in the Examples, suggest that the CD28 receptor and its ligand, the B7 antigen, may function in vivo by mediating T cell interactions with other cells such as B cells. The functional consequences of these interactions may be induced or inhibited using ligands that bind to the native CD28 receptor or the B7 antigen.

It is expected that administration of the B7 antigen will result in effects similar to the use of anti-CD28 monoclonal antibodies (mAbs) reactive with the CD28 receptor in vivo.

Thus, because anti-CD28 mAbs may exert either stimulatory or inhibitory effects on T cells, depending, in part, on the degree of crosslinking or "aggregation" of the CD28 receptor (Damle, *J. Immunol.* 140:1753–1761 (1988); Ledbetter et al., *Blood* 75(7):1531–1539 (1990)) it is expected that the B7 antigen, its fragments and derivatives, will act to stimulate or inhibit T cells in a manner similar to the effects observed for an anti-CD28 monoclonal antibody, under similar conditions in vivo. For example, administration of B7 antigen, e.g. as a soluble B7Ig fusion protein to react with CD28 positive T cells, will bind the CD28 receptor on the T cells and result in inhibition of the functional responses of T cells. Under conditions where T cell interactions are occurring as a result of contact between T cells and B cells, binding of introduced B7 antigen in the form of a fusion protein that binds to CD28 receptor on CD28 positive T cells should interfere, i.e. inhibit, the T cell interactions with B cells. Likewise, administration of the CD28 antigen, or its fragments and derivatives in vivo, for example in the form of a soluble CD28Ig fusion protein, will result in binding of the soluble CD28Ig to B7 antigen, preventing the endogenous stimulation of CD28 receptor by B7 positive cells such as activated B cells, and interfering with the interaction of B7 positive cells with T cells.

Alternatively, based on the known effects of aggregating the CD28 receptor, either by reacting T cells with immobilized ligand, or by crosslinking as described by Ledbetter et al., *Blood* 75(7):1531–1539 (1990)), the B7 antigen, and/or its fragments or derivatives, may be used to stimulate T cells, for example by immobilizing B7 antigen or B7Ig fusion protein, for reacting with the T cells. The activated T cells stimulated in this manner in vitro may be used in vivo in adoptive therapy.

Therefore, the B7 antigen and/or fragments or derivatives of the antigen may be used to react with T cells to regulate immune responses mediated by functional T cell responses to stimulation of the CD28 receptor. The B7 antigen may be presented for reaction with CD28 positive T cells in various forms. Thus, in addition to employing activated B cells expressing the B7 antigen, the B7 antigen may be encapsulated, for example in liposomes, or using cells that have been genetically engineered, for example using gene transfer, to express the antigen for stimulation of the CD28 receptor on T cells.

The CD28 receptor, and/or its fragments or derivatives, may also be used to react with cells expressing the B7 antigen, such as B cells. This reaction will result in inhibition of T cell activation, and inhibition of T cell dependent B cell responses, for example as a result of inhibition of T cell cytokine production.

In an additional embodiment of the invention, other reagents, such as molecules reactive with B7 antigen or the CD28 receptor are used to regulate T and/or B cell responses. For example, antibodies reactive with the CD28Ig fusion proteins, and Fab fragments of CD28Ig, may be prepared using the CD28Ig fusion protein as immunogen, as described above. These anti-CD28 antibodies may be screened to identify those capable of inhibiting the binding of the B7 antigen to CD28 antigen. The antibodies or antibody fragments such as Fab fragments may then be used to react with the T cells, for example, to inhibit CD28 positive T cell proliferation. The use of Fab fragments of the 9.3 monoclonal antibody, or Fab fragments of the anti-CD28Ig monoclonal antibodies as described herein, is expected to prevent binding of CD28 receptor on T cells to B7 antigen, for example on B cells. This will result in inhibition of the functional response of the T cells.

Similarly, anti-B7 monoclonal antibodies such as BB-1 mAb, or anti-B7Ig monoclonal antibodies prepared as described above using B7Ig fusion protein as immunogen, may be used to react with B7 antigen positive cells such as B cells to inhibit B cell interaction via the B7 antigen with CD28 positive T cells.

In another embodiment the B7 antigen may be used to identify additional compounds capable of regulating the interaction between the B7 antigen and the CD28 antigen. Such compounds may include soluble fragments of the B7 antigen or CD28 antigen or small naturally occurring molecules that can be used to react with B cells and/or T cells. For example, soluble fragments of the ligand for CD28 containing the extracellular domain (e.g. amino acids 1–215) of the B7 antigen may be tested for their effects on T cell proliferation.

Uses In Vitro and In Vivo

In a method of the invention, the ligand for CD28, B7 antigen, is used for regulation of CD28 positive (CD28$^+$) T cells. For example, the B7 antigen is reacted with T cells in vitro to crosslink or aggregate the CD28 receptor, for example using CHO cells expressing B7 antigen, or immobilizing B7 on a solid substrate, to produce activated T cells for administration in vivo for use in adoptive therapy. In adoptive therapy T lymphocytes are taken from a patient and activated in vitro with an agent. The activated cells are then reinfused into the autologous donor to kill tumor cells (see Rosenberg et al., *Science* 223:1318–1321 (1986)). The method can also be used to produce cytotoxic T cells useful in adoptive therapy as described in copending U.S. patent application Ser. No. 471,934, filed Jan. 25, 1990, incorporated by reference herein.

Alternatively, the ligand for CD28, its fragments or derivatives, may be introduced in a suitable pharmaceutical carrier in vivo, i.e. administered into a human subject for treatment of pathological conditions such as immune system diseases or cancer. Introduction of the ligand in vivo is expected to result in interference with T cell/B cell interactions as a result of binding of the ligand to T cells. The prevention of normal T cell/B cell contact may result in decreased T cell activity, for example, decreased T cell proliferation.

In addition, administration of the B7 antigen in vivo is expected to result in regulation of in vivo levels of cytokines, including, but not limited to, interleukins, e.g. interleukin ("IL")-2, IL-3, IL-4, IL-6, IL-8, growth factors including tumor growth factor ("TGF"), colony stimulating factor ("CSF"), interferons ("IFNs"), and tumor necrosis factor ("TNF") to promote desired effects in a subject. It is anticipated that ligands for CD28 such as B7Ig fusion proteins and Fab fragments may thus be used in place of cytokines such as IL-2 for the treatment of cancers in vivo. For example, when the ligand for CD28 is introduced in vivo it is available to react with CD28 antigen positive T cells to mimic B cell contact resulting in increased production of cytokines which in turn will interact with B cells.

Under some circumstances, as noted above, the effect of administration of the B7 antigen, its fragments or derivatives in vivo is stimulatory as a result of aggregation of the CD28 receptor. The T cells are stimulated resulting in an increase in the level of T cell cytokines, mimicking the effects of T cell/B cell contact on triggering of the CD28 antigen on T cells. In other circumstances, inhibitory effects may result from blocking by the B7 antigen of the CD28 triggering resulting from T cell/B cell contact. For example, the B7 antigen may block T cell proliferation. Introduction of the B7 antigen in vivo will thus produce effects on both T and B cell mediated immune responses. The ligand may also be administered to a subject in combination with the introduction of cytokines or other therapeutic reagents. Alternatively, for cancers associated with the expression of B7 antigen, such as B7 lymphomas, carcinomas, and T cell leukemias, ligands reactive with the B7 antigen, such as anti-B7Ig monoclonal antibodies, may be used to inhibit the function of malignant B cells.

Because CD28 is involved in regulation of the production of several cytokines, including TNF and gamma interferon (Lindsten et al., supra, (1989)), the ligand for CD28 of the invention may be useful for in vivo regulation of cytokine levels in response to the presence of infectious agents. For example, the ligand for CD28 may be used to increase antibacterial and antiviral resistance by stimulating tumor necrosis factor (TNF) and IFN production. TNF production seems to play a role in antibacterial resistance at early stages of infection (Havell, *J. Immunol.* 143:2894–2899 (1990)). In addition, because herpes virus infected cells are more susceptible to TNF-mediated lysis than uninfected cells (Koff and Fann, *Lymphokine Res.* 5:215 (1986)), TNF may play a role in antiviral immunity.

Gamma interferon is also regulated by CD28 (Lindsten et al., supra). Because mRNAs for alpha and beta IFNs share potential regulatory sequences in their 3' untranslated regions with cytokines regulated by CD28, levels of these cytokines may also be regulated by the ligand for CD28. Thus, the ligand for CD28 may be useful to treat viral diseases responsive to interferons (De Maeyer and De Maeyer-Guignard, in Interferons and Other Regulatory Cytokines, Wiley Publishers, New York (1988)). Following the same reasoning, the ligand for CD28 may also be used to substitute for alpha-IFN for the treatment of cancers, such as hairy cell leukemia, melanoma and renal cell carcinoma (Goldstein and Laszio, *CA: a Cancer Journal for Clinicians* 38:258–277 (1988)), genital warts and Kaposi's sarcoma.

In addition, B7Ig fusion proteins as described above may be used to regulate T cell proliferation. For example, the soluble CD28Ig and B7Ig fusion proteins may be used to block T cell proliferation in graft versus host (GVH) disease which accompanies allogeneic bone marrow transplantation. The CD28-mediated T cell proliferation pathway is cyclosporine-resistant, in contrast to proliferation driven by the CD3/Ti cell receptor complex (June et al., 1987, supra). Cyclosporine is relatively ineffective as a treatment for GVH disease (Storb, *Blood* 68:119–125 (1986)). GVH disease is thought to be mediated by T lymphocytes which express CD28 antigen (Storb and Thomas, *Immunol. Rev.* 88:215–238 (1985)). Thus, the B7 antigen in the form of B7Ig fusion protein, or in combination with immunosuppressants such as cyclosporine, for blocking T cell proliferation in GVH disease. In addition, B7Ig fusion protein may be used to crosslink the CD28 receptor, for example by contacting T cells with immobilized B7Ig fusion protein, to assist in recovery of immune function after bone marrow transplantation by stimulating T cell proliferation.

The fusion proteins of the invention may be useful to regulate granulocyte macrophage colony stimulating factor (GM-CSF) levels for treatment of cancers (Brandt et al., *N. Eng. J. Med.* 318:869–876 (1988)), AIDS (Groopman et al., *N. Eng. J. Med.* 317:593–626 (1987)) and myelodysplasia (Vadan-Raj et al., *N. Eng. J. Med.* 317:1545–1551 (1987)).

Regulation of T cell interactions by the methods of the invention may thus be used to treat pathological conditions such as autoimmunity, transplantation, infectious diseases and neoplasia.

In a preferred embodiment, the role of CD28-mediated adhesion in T cell and B cell function was investigated using procedures used to demonstrate intercellular adhesion mediated by MHC class I (Norment et al., (1988) supra) and class II (Doyle and Strominger, (1987) supra) molecules with the CD8 and CD4 accessory molecules, respectively. The CD28 antigen was expressed to high levels in Chinese hamster ovary (CHO) cells and the transfected cells were used to develop a CD28-mediated cell adhesion assay, described infra. With this assay, an interaction between the CD28 antigen and its ligand expressed on activated B lymphocytes, the B7 antigen, was demonstrated. The CD28 antigen, expressed in CHO cells, was shown to mediate specific intracellular adhesion with human lymphoblastoid and leukemic B cell lines, and with activated murine B cells. CD28-mediated adhesion was not dependent upon divalent cations. A mAb, BB-1, reactive with B7 antigen was shown to inhibit CD28-mediated adhesion. Transfected COS cells expressing the B7 antigen were also shown to adhere to $CD28^+$ CHO cells; this adhesion was blocked by mAbs to CD28 receptor and B7 antigen. The specific recognition by CD28 receptor of B7 antigen, indicated that B7 antigen is the ligand for the CD28 antigen.

The results presented herein also demonstrate that antibodies reactive with CD28 and B7 antigen specifically block helper $T_h$-mediated immunoglobulin production by allogeneic B cells, providing evidence of the role of CD28/B7 interactions in the collaboration between T and B cells.

In additional preferred embodiments, B7Ig and CD28Ig fusion proteins were constructed by fusing DNA encoding the extracellular domains of B7 antigen or the CD28 receptor to DNA encoding portions of human immunoglobulin C gamma 1. These fusion proteins were used to further demonstrate the interaction of the CD28 receptor and its ligand, the B7 antigen.

The cell adhesion assay method of the invention permits identification and isolation of ligands for target cell surface receptors mediating intercellular adhesion, particularly divalent cation independent adhesion. The target receptor may be an antigen or other receptor on lymphocytes such as T or B cells, on monocytes, on microorganisms such as viruses, or on parasites. The method is applicable for detection of ligand involved in ligand/receptor interactions where the affinity of the receptor for the ligand is low, such that interaction between soluble forms of the ligand and target receptor is difficult to detect. In such systems, adhesion interactions between other ligands and receptors that are divalent cation dependent may "mask" other interactions between ligands for target receptors, such that these interactions are only observed when divalent cations are removed from the system.

The cell adhesion assay utilizes cells expressing target cell surface receptor and cells to be tested for the presence of ligand mediating adhesion with the receptor. The cells expressing target receptor may be cells that are transfected with the receptor of interest, such as Chinese hamster ovary (CHO) or COS cells. The cells to be tested for the presence of ligand are labeled, for example with $^{51}Cr$, using standard methods and are incubated in suitable medium containing a divalent cation chelating reagent such as ethylenediamine tetraacetic acid (EDTA) or ethyleneglycol tetraacetic acid (EGTA). Alternatively, the assay may be performed in medium that is free of divalent cations, or is rendered free of divalent cations, using methods known in the art, for example using ion chromatography. Use of a divalent cation chelating reagent or cation-free medium removes cation-dependent adhesion interactions permitting detection of divalent cation-independent adhesion interactions. The labeled test cells are then contacted with the cells expressing target receptor and the number of labeled cells bound to the cells expressing receptor is determined by measuring the label, for example using a gamma counter. A suitable control for specificity of adhesion can be used, such as a blocking antibody, which competes with the ligand for binding to the target receptor.

The following examples are presented to illustrate the present invention and to assist one of ordinary skill in making and using the same. The examples are not intended in any way to otherwise limit the scope of the disclosure or the protection granted by Letters Patent hereon.

EXAMPLE 1

Identification of the Ligand for CD28 Receptor

If CD28 receptor antigen binds to a cell surface ligand, then cells expressing the ligand should adhere more readily to cells expressing CD28 receptor than to cells which do not. To test this, a cDNA clone encoding CD28 under control of a highly active promoter (Aruffo and Seed, (1987) supra) together with a selectable marker (pSV2dhfr) (Mulligan and Berg, Science 209:1414–1422 (1980)) was transfected into dihydrofolate reductase (dhfr)-deficient CHO cells.

Cell Culture

T51, 1A2, 5E1, Daudi, Raji, Jijoye, CEM, Jurkat, HSB2, THP-1 and HL60 cells (Bristol-Myers Squibb Pharmaceutical Research Institute, Seattle, Wash.) were cultured in complete RPMI medium (RPMI containing 10% fetal bovine serum (FBS), 100 U/ml penicillin and 100 µg/ml streptomycin. Dhfr-deficient Chinese hamster ovary (CHO) cells (Urlaub and Chasin, Proc. Natl. Acad Sci., 77:4216–4220 (1980)) were cultured in Maintenance Medium (Ham's F12 medium (GIBCO, Grand Island, N.Y.) supplemented with 10% FBS, 0.15 mM L-proline, 100 U/ml penicillin and 100 µg/ml streptomycin). Dhfr-positive transfectants were selected and cultured in Selective Medium (DMEM, supplemented with 10% FBS, 0.15 mM L-proline, 100 U/ml penicillin and 100 µg/ml streptomycin).

Spleen B cells were purified from Balb/c mice by treatment of total spleen cells with an anti-Thy 1.2 mAb (30H12) (Ledbetter and Herzenberg, Immunol. Rev. 47:361–389 (1979)) and baby rabbit complement. The resulting preparations contained approximately 85% B cells, as judged by FACS$^R$ analysis following staining with fluorescein isothiothiocyanate (FITC)-conjugated goat anti-mouse immunoglobulin (TAGO). These cells were activated by treatment for 72 hrs with E. coli lipopolysaccharide (LPS, List Biological Laboratories, Campbell, Calif.) at 10 µg/ml in complete RPMI.

Monoclonal Antibodies

Monoclonal antibody (mAb) 9.3 (anti-CD28) (ATCC No. HB 10271, Hansen et al., Immunogenetics 10:247–260 (1980)) was purified from ascites before use. mAb 9.3 F(ab')$_2$ fragments were prepared as described by Parham, in J. Immunol. 131:2895–2902 (1983). Briefly, purified mAb 9.3 was digested with pepsin at pH 4.1 for 75 min. followed by passage over protein A Sepharose to remove undigested mAb. A number of mAbs to B cell-associated antigens were screened for their abilities to inhibit CD28-mediated adhesion. mAbs 60.3 (CD18); 1F5 (CD20); G29-5 (CD21); G28-7, HD39, and HD6 (CD22); HD50 (CD23); KB61 (CD32); G28-1 (CD37); G28-10 (CD39); G28-5 (CD40); HERMES1 (CD44); 9.4 (CD45); LB-2 (CD54) and 72F3 (CD71) have been previously described and characterized in International Conferences on Human Leukocyte Differentiation Antigens I–III (Bernard et al., Eds., Leukocyte Typing, Springer-Verlag, New York (1984); Reinherz et al., Eds., Leukocyte Typing II Vol. 2 New York (1986); and McMichael et al., Eds., Leukocyte Typing III Oxford Univ. Press, New York, (1987)). These mAbs were purified before use by protein A Sepharose chromatography or by salt precipitation and in exchange chromatography. δTA401 (Kuritani and Cooper, J. Exp. Med. 155:839–848 (1982)) (Anti-IgD); 2C3 (Clark et al., (1986), supra) (anti-IgM); Namb1, H1DE, P10.1, W6/32 (Clark et al., (1986) supra; and Gilliland et al., Human Immunology 25:269–289 (1989), anti-human class I); and HB10A (Clark et al., (1986), supra, anti-MHC class II) were also purified before use. mAbs B43 (CD19); BL-40 (CD72); AD2, 1E9.28.1, and 7G2.2.11 (CD73); EBU-141, LN1 (CDw75); CRIS-1 (CD-76); 424/4A11, 424/3D9 (CD77) Leu 21, Ba, 1588, LO-panB-1, FN1, and FN4 (CDw78); and M9, G28-10, HuLym10, 2–7, F2B2.6, 121, L26, HD77, NU-B1, BLAST-1, BB-1, anti-BL7, anti-HC2, and L23 were used as coded samples provided to participants in the Fourth International Conference on Human Leukocyte Differentiation Antigens (Knapp, Ed., Leukocyte Typing IV, Oxford Univ. Press, New York (1990). These were used in ascites form. mAbs BB-1 and LB-1 (Yokochi et al., (1982) supra) were also purified from ascites before use. Anti-integrin receptor mAbs P3E3, P4C2, P4G9 (Wayner et al., J. Cell. Biol. 109:1321–1330 (1989)) were used as hybridoma culture supernatants.

Immunostaining Techniques

For indirect immunofluorescence, cells were incubated with mAbs at 10 µg/ml in complete RPMI for 1 hr at 4° C. mAb binding was detected with a FITC-conjugated goat anti-mouse immunoglobulin second step reagent. For direct binding experiments, mAbs 9.3 and BB-1 were directly conjugated with FITC as described by Goding in Monoclonal Antibodies: Principles and Practices Academic Press, Orlando, Fla. (1983), and were added at saturating concentrations in complete RPMI for 1 hr at 4° C. Nonspecific binding of FITC-conjugated mAbs was measured by adding the FITC conjugate following antigen pre-blocking (20–30 min at 4° C.) with unlabeled mAb 9.3 or BB-1. Immunohistological detection of adherent lymphoblastoid cells was achieved using the horseradish peroxidase (HRP) method described by Hellstrom et al., J. Immunol. 127:157–160 (1981).

Plasmids and Transfections cDNA clones encoding the amino acid sequences corresponding to T cell antigens CD4, CD5 and CD28 in the expression vector pπH3M (Aruffo and Seed (1987), supra)), were provided by Drs. S. Aruffo and B. Seed, Massachusetts General Hospital, Boston, Mass. An expressible cDNA clone in the vector CDM8 encoding the amino acid sequence corresponding to B7 antigen (Freeman et al., J. Immunol. 143:2714–2722 (1989)) was provided by Dr. Gordon Freeman (Dana Farber Cancer Institute, Boston, Mass.).

Dhfr-deficient CHO cells were co-transfected with a mixture of 9 µg of plasmid πH3M-CD28 (Aruffo and Seed, (1987) supra) and 3 µg of plasmid pSV2dhfr (Mulligan and Berg, (1980), supra) using the calcium phosphate technique (Graham and Van Der Eb, Virology 52:456–467 (1973)). Dhfr-positive colonies were isolated and grown in Selective Medium containing increasing amounts of methotrexate (Sigma Chemical Co., St. Louis, Mo.). Cells resistant to 10 mM methotrexate were collected by incubation in PBS containing 10 mM EDTA, stained for presence of the CD28 receptor by indirect immunofluorescence, and separated by FACS$^R$ into CD28-positive (CD28$^+$) and CD28-negative (CD28$^-$) populations. Both populations were again cultured in Selective Medium containing increasing concentrations of methotrexate to 1 µM, stained for the CD28 antigen and again sorted into CD28$^+$ and CD28$^-$ populations.

COS cells were transfected with B7, CD4 or CD5 cDNAs as described by Malik et al., *Molecular and Cellular Biology* 9:2847–2853 (1989). Forty-eight to seventy-two hours after transfection, cells were collected by incubation in PBS containing 10 mM EDTA, and used for flow cytometry analysis or in CD28-mediated adhesion assays as described, infra.

Cell lines expressing high ($CD28^+$) and low ($CD28^-$) levels of the CD28 receptor were isolated from amplified populations by $FACS^R$ sorting following indirect immunostaining with mAb 9.3. After two rounds of $FACS^R$ selection, the $CD28^+$ population stained uniformly positive with FITC-conjugated mAb 9.3 (mean channel, 116 in linear fluorescence units), while the $CD28^-$ population stained no brighter (mean channel, 3.9) than unstained cells (mean channel, 3.7). Staining by $CD28^+$ CHO cells was approximately ten-fold brighter than phytohemagglutin-stimulated T cells (mean channel, 11.3). The $CD28^+$ and $CD28^-$ populations stably maintained their phenotypes after more than 6 months of continuous culture in Selective Medium containing 1 $\mu$M of methotrexate.

Cell Adhesion Assay for a Ligand for CD28

An adhesion assay to detect differential binding to $CD28^+$ and $CD28^-$ CHO cells by cells expressing a ligand for CD28 was developed. Since mAb 9.3 has been shown to inhibit mixed lymphocyte reactions using B lymphoblastoid cells lines as a source of alloantigen (Damle et al., (1981) supra; and Lesslauer et al., *Eur. J. Immunol.* 16:1289–1296 (1986)) B lymphoblastoid cell lines were initially tested for CD28-mediated adhesion.

CD28-Mediated Adhesion Assay

Cells to be tested for adhesion were labeled with $^{51}Cr$ (0.2–1 mCi) to specific activities of 0.2–2 cpm/cell. A mouse mAb having irrelevant specificity, mAb W1, directed against human breast carcinoma-associated mucin, (Linsley et al., *Cancer Res.* 46:5444–5450 (1986)), was added to the labeling reaction to a final concentration of 100 $\mu$g/ml to saturate Fc receptors. Labeled and washed cells were preincubated in complete RPMI containing 10 $\mu$g/ml of mAb W1, and unless otherwise indicated, 10 mM EDTA. mAb 9.3 or mAb 9.3 $F(ab')_2$ was added to some samples at 10 $\mu$g/ml, for approximately 1 hr at 23° C.

Labeled cells (1–10×$10^6$/well in a volume of 0.2 ml complete RPMI, containing EDTA and mAbs, where indicated) were then added to the CHO monolayers. Adhesion was initiated by centrifugation in a plate carrier (1,000 rpm, in a Sorvall HB1000 rotor, approximately 210×g) for 3 min at 4° C. Plates were then incubated at 37° C. for 1 hr. Reactions were terminated by aspirating unbound cells and washing five times with cold, complete RPMI. Monolayers were solubilized by addition of 0.5 N NaOH, and radioactivity was measured in a gamma counter. For most experiments, numbers of bound cells were calculated by dividing total bound radioactivity (cpm) by the specific activity (cpm/cell) of labeled cells. When COS cells were used, their viability at the end of the experiment was generally less than 50%, so specific activity calculations were less accurate. Therefore, for COS cells results are expressed as cpm bound.

In pilot experiments, T51 lymphoblastoid cells were found to adhere more to $CD28^+$ CHO cells, than to $CD28^-$ CHO cells. Furthermore, adhesion of T51 cells to $CD28^+$ CHO cells was partially blocked by mAb 9.3, while adhesion to $CD28^-$ CHO cells was not consistently affected. Adhesion was not affected by control mAb L6 (ATCC No. HB 8677, Hellstrom et al., *Cancer Res.* 46:3917–3923 (1986)), which is of the same isotype as mAb 9.3 (IgG2a).

These experiments suggested that T51 cells adhered specifically to $CD28^+$ CHO cells. Since blocking of adhesion by mAb 9.3 was incomplete, ways to increase the specificity of the CD28 adhesion assay were explored.

The effects of divalerit cation depletion on T51 cell adhesion to $CD28^+$ and $CD28^-$ CHO cells were examined. Preliminary experiments showed that EDTA treatment caused loss of CHO cells during washing, so the CHO cell monolayers were fixed with paraformaldehyde prior to EDTA treatment. Fixation did not significantly affect CD28-mediated adhesion by T51 cells either in the presence or absence of mAb 9.3. Monolayers of $CD28^+$ and $CD28^-$ CHO cells (1 to 1.2×$10^5$/$cm^2$ in 48 well plastic dishes) were fixed in 0.5% paraformaldehyde for 20 min at 23° C., washed and blocked in Complete RPMI for 1 hr, then pre-incubated with or without mAb 9.3 or mAb 9.3 $F(ab')_2$ at 10 $\mu$g/ml in Complete RPMI for 1 hr at 37° C. T51 cells were labeled with $^{51}Cr$, preincubated with or without 10 mM EDTA, added to CHO cells and cellular adhesion was measured. The results are presented in FIG. 1. Mean and standard deviation (error bars) are shown for three replicate determinations.

Figure 2:
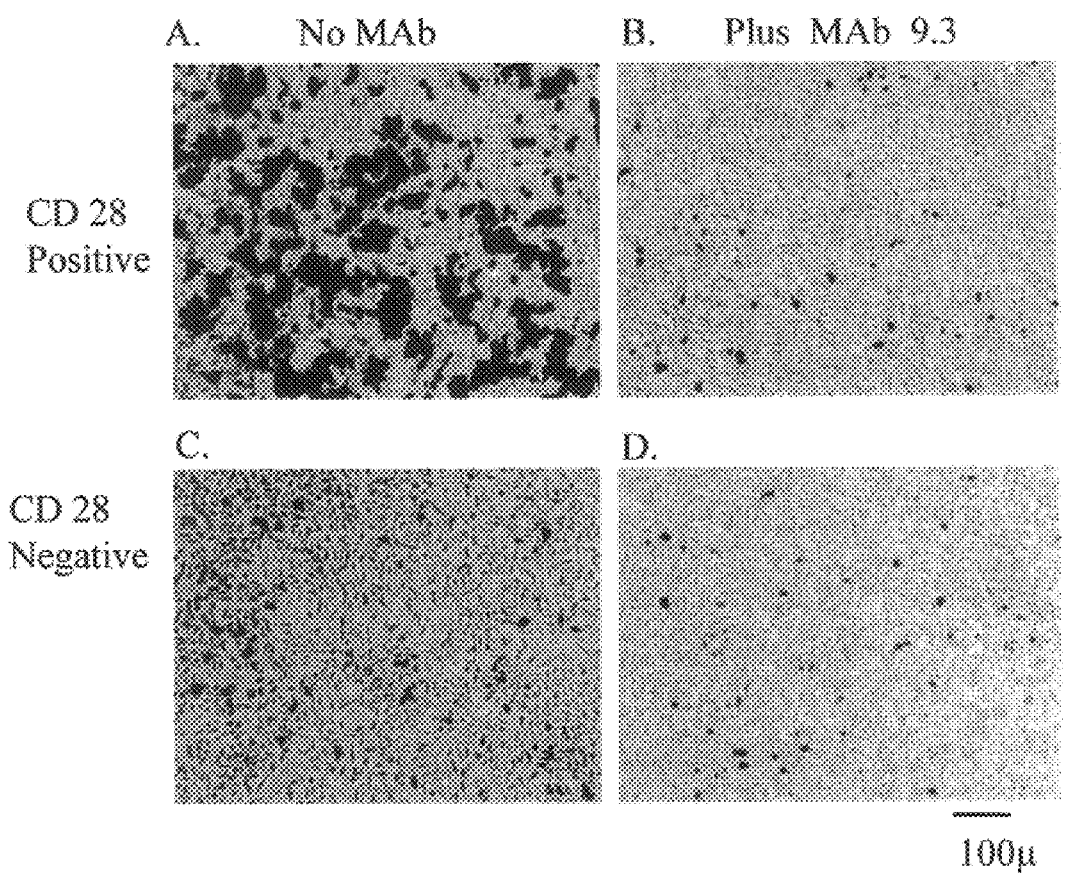
FIG. 2 are micrographs of the cellular adhesion studies of FIG. 1, as described in Example 1, infra.

The specificity of CD28-mediated adhesion was greatly increased in the presence of EDTA (FIG. 1). Adhesion to $CD28^+$ cells in the presence of EDTA was 17-fold greater than to $CD28^{31}$ cells in the presence of EDTA, compared with 5.5-fold greater in its absence. Adhesion to $CD28^+$ cells in the presence of mAb 9.3 plus EDTA was reduced by 93%, compared with 62% in the presence of mAb alone. CD28-mediated adhesion of T51 cells in the presence of EDTA could also be seen quite clearly by microscopic examination following immunohistological staining of T51 cells. Cellular adhesion between unlabeled T51 cells and $CD28^+$ or $CD28^-$ CHO cells was determined in the presence of 10 mM EDTA as described above. Adherent T51 cells were stained with biotinylated anti-human Class II Ab, HB10a, fixed with 0.2% glutaraldehyde and visualized by sequential incubation with avidin-conjugated HRP (Vector Laboratories, Inc., Burlingame, Calif.) and diaminobenzidine solution (Hellstrom and Hellstrom, *J. Immunol.* 127:157–160 (1981)). The results of staining are shown in FIG. 2. A similar, but slightly less significant increase in adhesion specificity, was also observed in the presence of the calcium-specific chelator, EGTA.

The Ligand for CD28 is a B Cell Activation Marker

Figure 3:
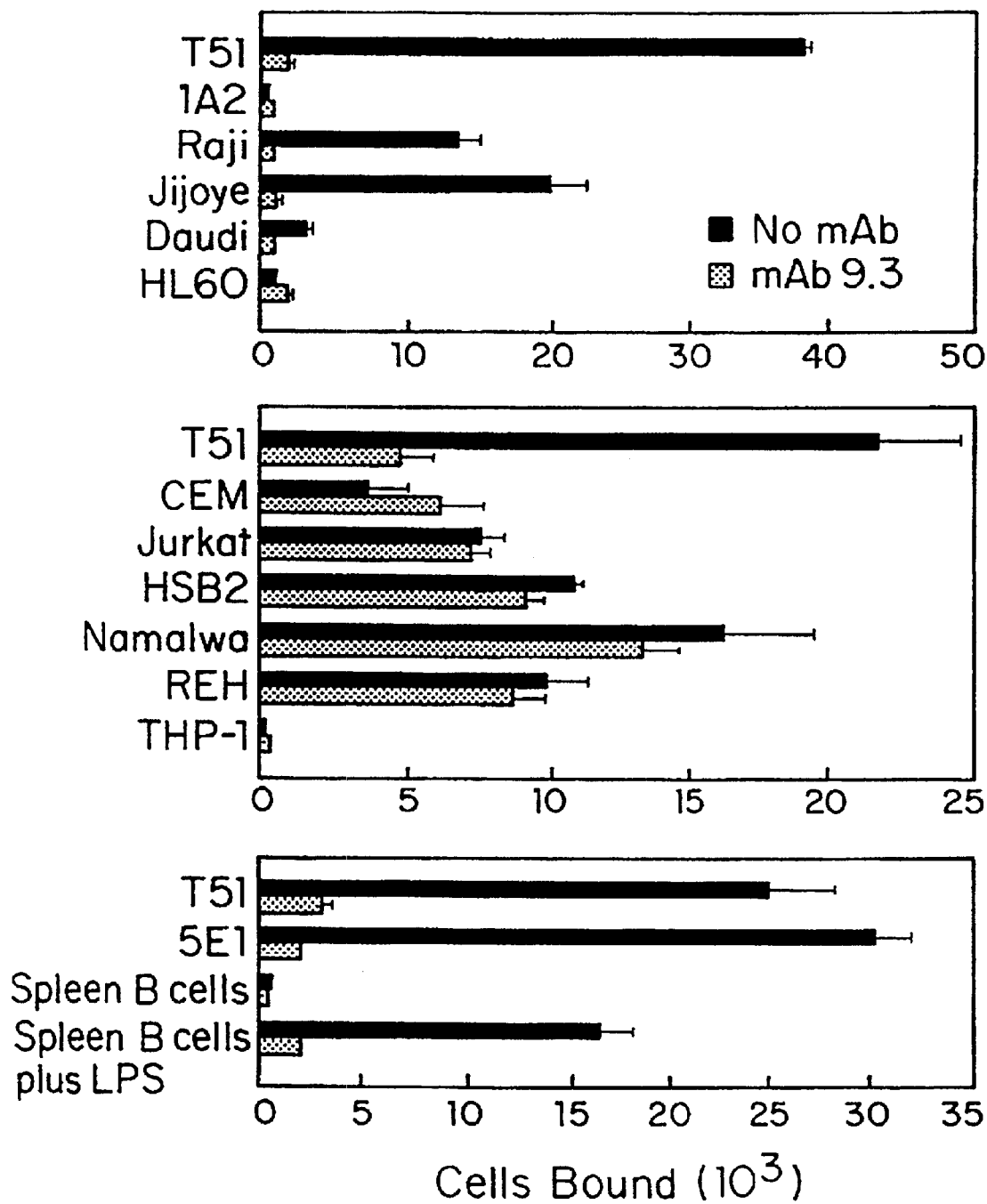
FIG. 3 are bar graphs of experiments testing the ability of different human cell lines and normal and activated murine spleen B cells to adhere to CD28$^+$ CHO cells, as described in Example 1, infra.

The increased specificity of CD28-mediated adhesion in EDTA made it possible to more readily detect adhesion by cells other than T51. A number of additional cell lines were tested, including three lymphoblastoid lines (T51, 1A2, and 5E1); four Burkett's Lymphoma lines (Daudi, Raji, Jijoye, and Namalwa); one acute lymphoblastic (B cell) leukemia (REH); three T cell leukemias (CEM, Jurkat and HSB2); and two monocytic leukemias (THP-1 and HL60). As a source of primary B cells, murine splenic B cells, before and after activation with LPS, were tested. All cells were tested for adhesion to both $CD28^+$ and $CD28^-$ CHO cells, in the absence and presence of MAb 9.3. The cells were labeled with $^{51}Cr$ and CD28-mediated adhesion was measured as described above. Three representative experiments showing adhesion to $CD28^+$ CHO cells are shown in FIG. 3. Inhibition by mAb 9.3 is shown as an indicator of specificity; in most cases, adhesion measured in the presence of mAb 9.3 was approximately equal to adhesion to $CD28^+$ cells.

CD28-specific adhesion (i.e., adhesion being greater than 70% inhibitable by mAb 9.3), was observed with T51, 5E1, Raji, and Jijoye cells. Daudi cells also showed specific adhesion, although to a lesser extent. Other cell lines did not show specific CD28-mediated adhesion, although some (e.g., Namalwa) showed relatively high non-specific adhesion. Primary mouse splenic B cells did not show CD28-mediated adhesion, but acquired the ability to adhere following activation with LPS. In other experiments, six additional lymphoblastoid lines showed CD28-mediated adhesion, while the U937 cell line, unstimulated human tonsil B cells, and phytohemagglutinin stimulated T cells did not show adhesion. These experiments indicate that a ligand for CD28 is found on the cell surface of activated B cells of human or mouse origin.

CD28-Mediated Adhesion is Specifically Blocked by a mAb (BB-1) to B7 Antigen

In initial attempts to define B cell molecules involved in CD28-mediated adhesion, adhesion by lymphoblastoid cell lines having mutations in other known cellular adhesion molecules was measured using the adhesion assay described above. The 616 lymphoblastoid line (MHC class II-deficient) (Gladstone and Pious, Nature 271:459–461 (1978)) bound to CD28$^+$ CHO cells equally well or better than parental T51 cells. Likewise, a CD18-deficient cell line derived from a patient with leukocyte adhesion deficiency (Gambaro cells) (Beatty et al., Lancet 1:535–537 (1984)) also adhered specifically to CD28. Thus, MHC class II and CD18 molecules do not mediate adhesion to CD28.

A panel of mAbs to B cell surface antigens were then tested for their ability to inhibit CD28-mediated adhesion of T51 cells. For these experiments, a total of 57 mAbs reactive with T51 cells were tested, including mAbs to the B cell-associated antigens CD19, CD20, CD21, CD22, CD23, CD37, CD39, CD40, CD71, CD72, CD73, CDw75, CD76, CD77, CDw78, IgM, and IgD; other non-lineage-restricted antigens CD18, CD32, CD45, CD54, and CD71; CD44 and another integrin; MHC class I and class II antigens; and 30 unclustered B cell associated antigens. In addition to these, many other mAbs which did not react with T51 by FACS$^R$ analysis were tested. Initial screening experiments were carried out in the absence of EDTA, and any mAbs which blocked adhesion were subsequently retested in the presence and absence of EDTA. Of these mAbs, only those directed against MHC class I molecules (Namb1, H1DE, P10.1, W6/32), and one to an unclustered B cell antigen (BB-1), originally described as a B cell activation marker (Yokochi et al. (1982) supra) were consistently able to block CD28-mediated adhesion by greater than 30%.

Figure 4:
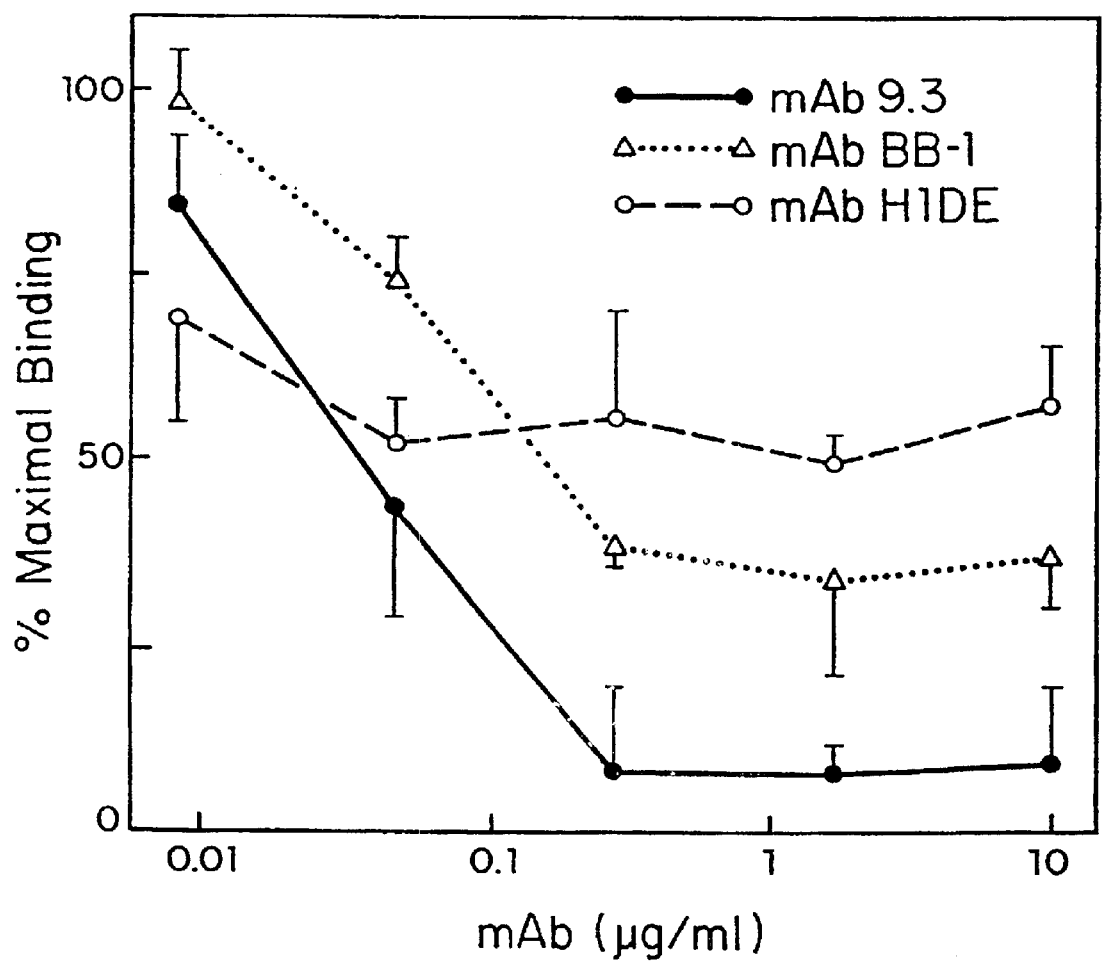
FIG. 4 is a graph of the effects of blocking by mAbs on CD28-mediated adhesion to human B cells, as described in Example 1, infra.

The dose-dependence of adhesion inhibition by the anti-Class I mAb, H1DE, by BB-1 and by 9.3 were compared in the presence of EDTA in the experiment shown in FIG. 4. Jijoye cells were labeled with $^{51}$Cr and allowed to adhere to CD28$^+$ CHO cells in the presence of 10 mM EDTA as described above. Adhesion measured in the presence of the indicated amounts of mAbs 9.3, H1DE (anti-human class I MHC, Gaur et al., Immunogenetics 27:356–361 (1988)), or mAb BB-1 is expressed as a percentage of maximal adhesion measured in the absence of mAb (45,000 cells bound). mAb 9.3 was most effective at blocking, but mAb BB-1 was able to block approximately 60% of adhesion at concentrations less than 1 μg/ml. mAb H1DE also partially blocked adhesion at all concentrations tested. When EDTA was omitted from the adhesion assay, blocking by class I mAbs was consistently less, and required higher mAb concentrations, than mAbs 9.3 or BB-1.

Binding of mAb BB-1 by Different Cells Correlates with CD28-Specific Adhesion

To investigate the roles of molecules recognized by anti-class I and BB-1 mAbs in CD28-mediated adhesion, levels of these antigens on certain of the cell lines tested for CD28-specific adhesion in FIG. 3 were compared. Cells were analyzed by FACS$^R$ following indirect immunofluorescence staining with mAbs H1DE and BB-1. Cell lines 1A2, Namalwa, REH and HL60 (which did not adhere specifically to CD28) all bound high levels of mAb H1DE, whereas Daudi cells (which did adhere) did not show detectable binding. Therefore, a direct correlation between CD28-mediated adhesion and expression of class I antigens was not observed. On the other hand, these experiments suggested a correlation between adhesion to CD28 and staining by mAb BB-1.

To confirm this correlation, cell lines examined for CD28-mediated adhesion in FIG. 3 were tested for staining by direct immunofluorescence using FITC-conjugated mAb BB-1 (Table 1). Cell lines were incubated with no mAb or with FITC-conjugated mAb BB-1 with or without preincubation with cold (unlabeled) BB-1 mAb. Values shown in Table 1 represent mean fluorescence in linear units. All of the cell lines which adhered specifically to CD28 receptor (FIG. 3) bound higher levels of the FITC-conjugate than those which did not adhere specifically. Antigen specificity was demonstrated in all cases by the ability of unlabeled mAb BB-1 to compete for binding of the FITC-conjugate.

TABLE 1

CELLS WHICH ADHERE TO CD28 RECEPTOR ALSO BIND mAb BB-1

| CELL LINE | TYPE[1] | NO mAb | FITC-BB-1 − COLD | FITC-BB-1 + COLD | SPECIFIC[4] BINDING |
|---|---|---|---|---|---|
| Positive for CD2B Adhesion[2] | | | | | |
| T51 | B-LCL | 2.3 | 16.4 | 3.0 | 13.4 |
| 5E1 | B-LCL | 2.1 | 13.0 | 2.4 | 10.6 |
| Jijoye | BL | 2.3 | 17.8 | 2.8 | 15.0 |
| Raji | BL | 2.1 | 7.1 | 2.8 | 4.3 |
| Daudi | BL | 2.1 | 6.4 | 2.8 | 3.6 |
| Negative for CD28 Adhesion[3] | | | | | |
| 1A2 | B-LCL | 2.1 | 4.5 | 4.3 | <1 |
| Namalwa | BL | 2.2 | 3.8 | 2.2 | 1.6 |
| REH | B-ALL | 2.0 | 2.1 | 2.0 | <1 |
| CEM | T-ALL | 2.3 | 2.0 | 1.9 | <1 |
| Jurkat | T-ALL | 2.2 | 2.2 | 2.0 | <1 |
| HSB2 | T-ALL | 2.1 | 2.3 | 2.3 | <1 |
| HL60 | AML | 2.3 | 3.1 | 3.1 | <1 |
| THP-1 | AML | 2.3 | 3.1 | 3.0 | <1 |

[1]B-LCL = B-lymphoblastoid cell line
BL = Burkett's lymphoma
B-ALL = B cell-derived acute lymphoblastoid leukemia
T-ALL = T cell-derived acute lymphoblastoid leukemia
AML = Acute Monocytic leukemia
[2]Positive for CD28 adhesion = >70% inhibition of adhesion by mAb 9.3
[3]Negative for CD28 Adhesion = <70% inhibition of adhesion by mAb 9.3.
[4]Specific binding = (FITC-BB-1 + cold) subtracted from (FITC BB-1 − cold).

COS Cells Expressing the B7 Antigen Adhere Specifically to CD28

Figure 5:
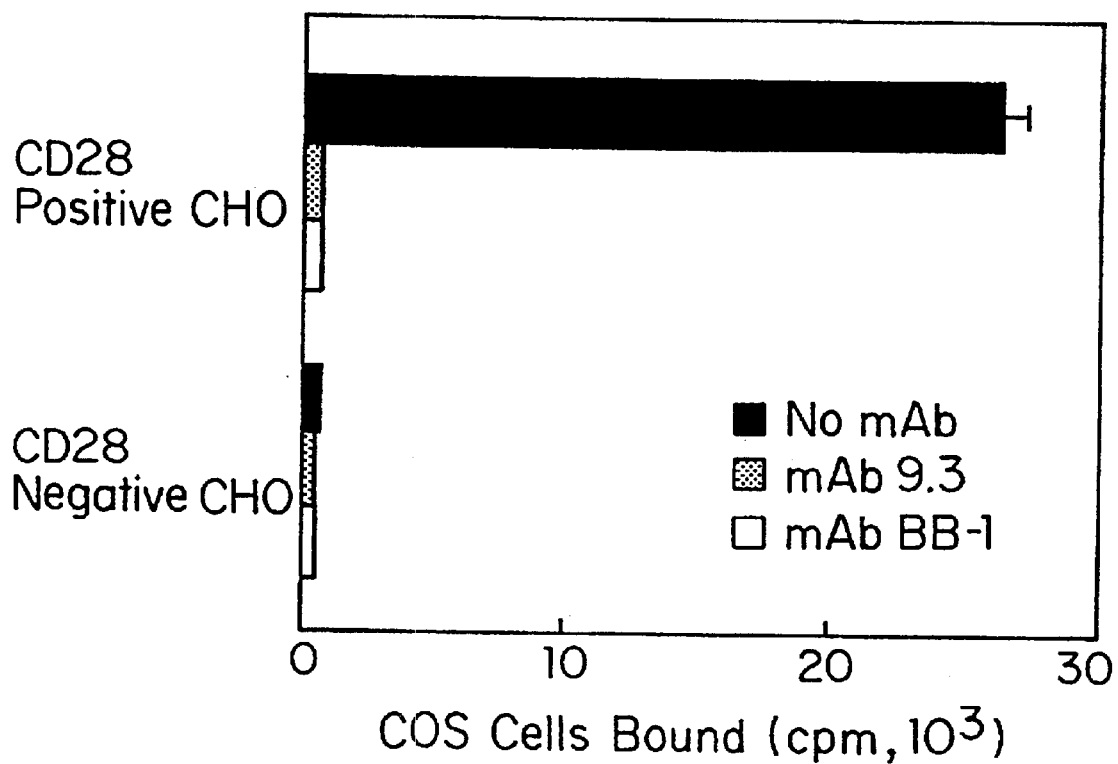
FIG. 5 is a bar graph of the results of adhesion between COS cells transfected with B7 antigen and CD28$^+$ or CD28$^-$ CHO cells, as described in Example 1, infra.

The role of the B7 antigen recognized by mAb BB-1 in CD28-mediated adhesion was investigated using a cDNA clone isolated and sequenced by Freeman et al. as described in J. Immunol. 143:2714–2722 (1989). COS cells were transfected with an expression vector containing the cDNA clone encoding the B7 antigen, as described by Freeman et al., (1989), supra as described above. Forty-eight hours later, transfected COS cells were removed from their dishes by incubation in PBS containing 10 mM EDTA, and were labeled with $^{51}$Cr. Cells were shown to express B7 antigen by FACS$^R$ analysis following indirect staining with mAb BB-1 as reported by Freeman et al, supra. Adhesion between B7 transfected COS cells and CD28$^+$ or CD28$^-$ CHO cells was then measured in the presence of 10 mM EDTA as described above. Where indicated, adhesion was measured in the presence of mAbs 9.3 or BB-1 (10 µg/ml). As shown in FIG. 5, B7/BB-1-transfected COS cells adhered readily to CD28$^+$ CHO cells; adhesion was completely blocked by both mAbs 9.3 and BB-1. No adhesion to CD28$^-$ CHO cells was detected. This experiment was repeated five times with identical results.

In other experiments, adhesion was not blocked by non-reactive, isotype matched controls, mAb W5 (IgM) (Linsley, (1986) supra) and mAb L6 (IgG2A) (Hellstrom et al., (1986) supra), or by mAb H1DE, which reacts with class I antigens on COS cells. CD28-mediated adhesion by B7 transfected cells could also be clearly seen by microscopic examination of the CHO cell monolayers after the assay. When COS cells were transfected with expressible CD4 or CD5 cDNA clones, no CD28-mediated adhesion was detected. Expression of CD4 and CD5 was confirmed by FACS$^R$ analysis following immunofluorescent staining. When EDTA was omitted from the assay, adhesion measured with CD5-transfected COS cells was greatly increased but not inhibited by mAb 9.3. In contrast, adhesion by B7 transfected COS cells under these conditions was still partially blocked (approximately 40%) by mAb 9.3. Thus, transfection of B7 into COS cells confers the ability on the cells to adhere specifically to CD28 receptor.

The above assay for intracellular adhesion mediated by the CD28 receptor, described above, demonstrated CD28-mediated adhesion by several lymphoblastoid and leukemic B cell lines, and by primary murine spleen cells following activation with LPS. These results indicate the presence of a natural ligand for the CD28 receptor on the cell surface of some activated B lymphocytes.

Several lines of evidence show that the B cell molecule which interacted with the CD28 receptor is the B7 antigen. mAb BB-1 was identified from a panel of mAbs as the mAb which most significantly inhibited CD28-mediated adhesion. Furthermore, a correlation was observed between the presence of B7 antigen and CD28-mediated adhesion (Table 1). Finally, COS cells transfected with B7 cDNA demonstrated CD28-mediated adhesion. Taken together, these observations provide strong evidence that B7 antigen is a ligand for CD28 receptor. Because both CD28 (Aruffo and Seed, (1987) supra) and B7 (Freeman et al., (1989) supra) are members of the immunoglobulin superfamily, their interaction represents another example of heterophilic recognition between members of this gene family (Williams and Barclay (1988), supra).

CD28-mediated adhesion differs in several respects from other cell adhesion systems as shown in the above results. CD28-mediated adhesion was not blocked by mAbs to other adhesion molecules, including mAbs to ICAM-1 (LB-2), MHC class II (HB10a) CD18 (60.3), CD44 (HERMES-1 homing receptor), and an integrin (P3E3, P4C2, P4G9). CD28-mediated adhesion was also resistant to EDTA and EGTA, indicating that this system does not require divalent cations, in contrast to integrins (Kishimoto et al., Adv. Immunol. 46:149–182 (1989)) and some homing receptors (Stoolman, Cell 56:907–910 (1989)) which require divalent cations. In the system described herein, in which CD28 receptor was expressed to high levels relative to those on activated T cells, it was sometimes difficult to measure CD28-mediated adhesion because of cation-dependent "background" adhesion (i.e., that not blocked by MAb 9.3, see FIG. 1). Preliminary experiments suggest that background adhesion in the absence of EDTA was also blocked by MAb 60.3, which inhibits adhesion mediated by LFA-1 (Pohlman et al., J. Immunol. 136:4548–4553 (1986)). Even under optimal conditions, some cells (such as Namalwa, see FIG. 3) showed significant non-CD28 dependent adhesion to CHO cells. Non-CD28 mediated adhesion systems may also be responsible for the incomplete blockage by mAb BB-1 of B cell adhesion (FIG. 4). That this mAb is more effective at blocking adhesion by transfected COS cells (FIG. 5) may indicate that non-CD28 mediated systems are less effective in COS cells.

Finally, CD28-mediated adhesion appears more restricted in its cellular distribution to T and B cells as compared to other adhesion molecules. CD28 receptor is primarily expressed by cells of the T lymphocyte lineage. The B7 antigen is primarily expressed by cells of the B lymphocyte lineage. Consistent with this distribution, the ligand for CD28 was only detected on cells of B lymphocyte lineage. Thus, available data suggest that CD28 mediates adhesion mainly between T cells and B cells. However, since CD28 expression has been detected on plasma cells (Kozbor et al., J. Immunol 138:4128–4132 (1987)) and B7 on cells of other lineages, such as monocytes (Freeman et al., (1989) supra), it is possible that other cell types may also employ this system. Many adhesion molecules are known to mediate T cell-B cell interactions during an immune response and the levels of several of these, including CD28 and B7 antigen, have been reported to increase following activation. Increased levels of these molecules may help explain why activated B cells are more effective at stimulating antigen-specific T cell proliferation than are resting B cells. Because the B7 antigen is not expressed on resting B cells, CD28-mediated adhesion may play a role in maintaining or amplifying the immune response, rather than initiating it. Such a role is also consistent with the function of CD28 in regulating lymphokine and cytokine levels (Thompson et al., (1989), supra; and Lindsten et al., (1989), supra).

EXAMPLE 2

Characterization of Interaction between CD28 Receptor and B7 Antigen

This example used alloantigen-driven maturation of B cells as a model system to demonstrate the involvement of the CD28 receptor on the surface of major histocompatibility complex (MHC) class II antigen-reactive CD4 positive T helper ($T_h$) cells and antigen presenting B cells during the $T_h$-B cell cognate interaction leading to B cell differentiation into immunoglobulin-secreting cells (IgSC).

Cognate interaction between CD4$^+$ $T_h$ and antigen-presenting B cells results in the activation and differentiation of both cell types consequently leading to the development of immunoglobulin-secreting cells (Moller (Ed) Immunol Rev. 99:1 (1987), supra). Allogenic MLR offers an ideal system to analyze cognate $T_h$-B cell interaction because alloantigen-specific CD4$^+$ $T_h$ induce both the activation and differentiation of alloantigen-bearing B cells into immunoglobulin secreting cells (Chiorazzi et al., Immunol Rev. 45:219 (1979); Kotzin et al., J. Immunol. 127:931 (1981); Friedman et al., J. Immunol. 129:2541 (1982); Goldberg et al., J. Immunol. 135:1012 (1985); and Crow et al., J. Exp. Med. 164:1760 (1986)). The involvement of the CD28 receptor on $T_h$ cells and its ligand B7 during the activation of $T_h$ and B cells in the allogeneic MLR was first examined using murine mAb directed at these molecules.

Culture Medium

Complete culture medium (CM) consisted of RPMI 1640 (Irvine Scientific, Santa Ana, Calif.) supplemented with 100

U/ml of penicillin G, 100 μg/ml of streptomycin, 2 mM L-glutamine, $5 \times 10^{-5}$ M 2-ME, and 10% FBS (Irvine Scientific).

Cells and mAbs

EBV-transformed B cell lines CESS (HLA-AS1, A3; B5, B17; DR7), JIJOYE, and SKW6.4 (HLA-A1a; B27, B51; DR7), were obtained from the ATCC. EBV-transformed B cell lines ARENT (HLA-A2; B38, B39, DRw6) and MSAB (HLA-A1, A2; B57; DR7) were provided by Dr. E. G. Engleman, Stanford University School of Medicine, Stanford, Calif. Hybridomas OKT4 (IgG anti-CD4), OKT8 (IgG anti-CD8) and HNK1 (IgM anti-CD57) were obtained from the ATCC and ascitic fluids from these hybridomas were generated in pristane-primed BALB/c mice. Production and characterization of anti-CD28 mAb 9.3 (IgG2a) has been described by Ledbetter et al., *J. Immunol.* 135:2331 (1985); Hara et al., *J. Exp. Med.* 161:1513 (1985) and Martin et al., *J. Immunol.* 136:3282 (1986), incorporated by reference herein. mAb 4H9 (IgG2a anti-CD7) as described by Damle and Doyle, *J. Immunol* 143:1761 (1989), incorporated by reference herein, was provided by Dr. Engleman and mAb anti-B7 antibody (BB1; IgM) as described by Tokochi et al., *J. Immunol.* 128:823 (1981), incorporated by reference herein, was provided by Dr. E. Clark, University of Washington, Seattle, Wash.

Peripheral blood mononuclear cells (PBMC) from healthy donors were separated into T and non-T cells using a sheep erythrocyte rosetting technique, and T cells were separated by panning into $CD4^+$ subset and further into $CD4^+$ $CD45RA-CD45RO^+$ memory subpopulation as described by Damle et al., *J. Immunol.* 139:1501 (1987), incorporated by reference herein.

Proliferative Responses of T Cells

To examine the effect of anti-CD28 and anti-B7 mAbs on the proliferative responses of T cells, fifty-thousand $CD4^+$ $CD45RO^+$ T cells were stimulated by culturing with $1 \times 10^4$ irradiated (8000 rad from a $^{137}Cs$ source) EBV-transformed allogenic B cells (or $2.5 \times 10^4$ non-T cells) in 0.2 ml of CM in round-bottom microtiter wells in a humidified 5% $CO_2$ and 95% air atmosphere in the presence of 10 μg/ml of mAb reactive with CD7, CD28, CD57 or B7 antigen. $CD4^+$ $CD45RO^+$ T cells also were also independently stimulated with 100 μg/ml of soluble purified protein derivative of tuberculin (PPD, Connough Laboratories, Willowdale, Ontario, Canada) in the presence of $1 \times 10^4$ irradiated (3000 rad) autologous non-T cells in the presence of the above mAbs. Triplicate cultures were pulsed with 1 μCi/well=37 kBq/well of [$^3$H]dThd (6.7 Ci/mmol, NEN, Boston, Mass.) for 16 h before harvesting of cells for measurement of radiolabel incorporation into newly synthesized DNA. The results are expressed as cpm±SEM. Proliferative responses were examined on day 7 of culture. EBV-transformed B cell lines were used as stimulator cells in these experiments because these B cells exhibit various features of activated B cells such as the expression of high levels of MHC class II and B7 molecules (Freeman-et al., *J. Immunol.* 139:3260 (1987); and Yokochi et al. *J. Immunol.* 128:823(1982).

Figure 6:
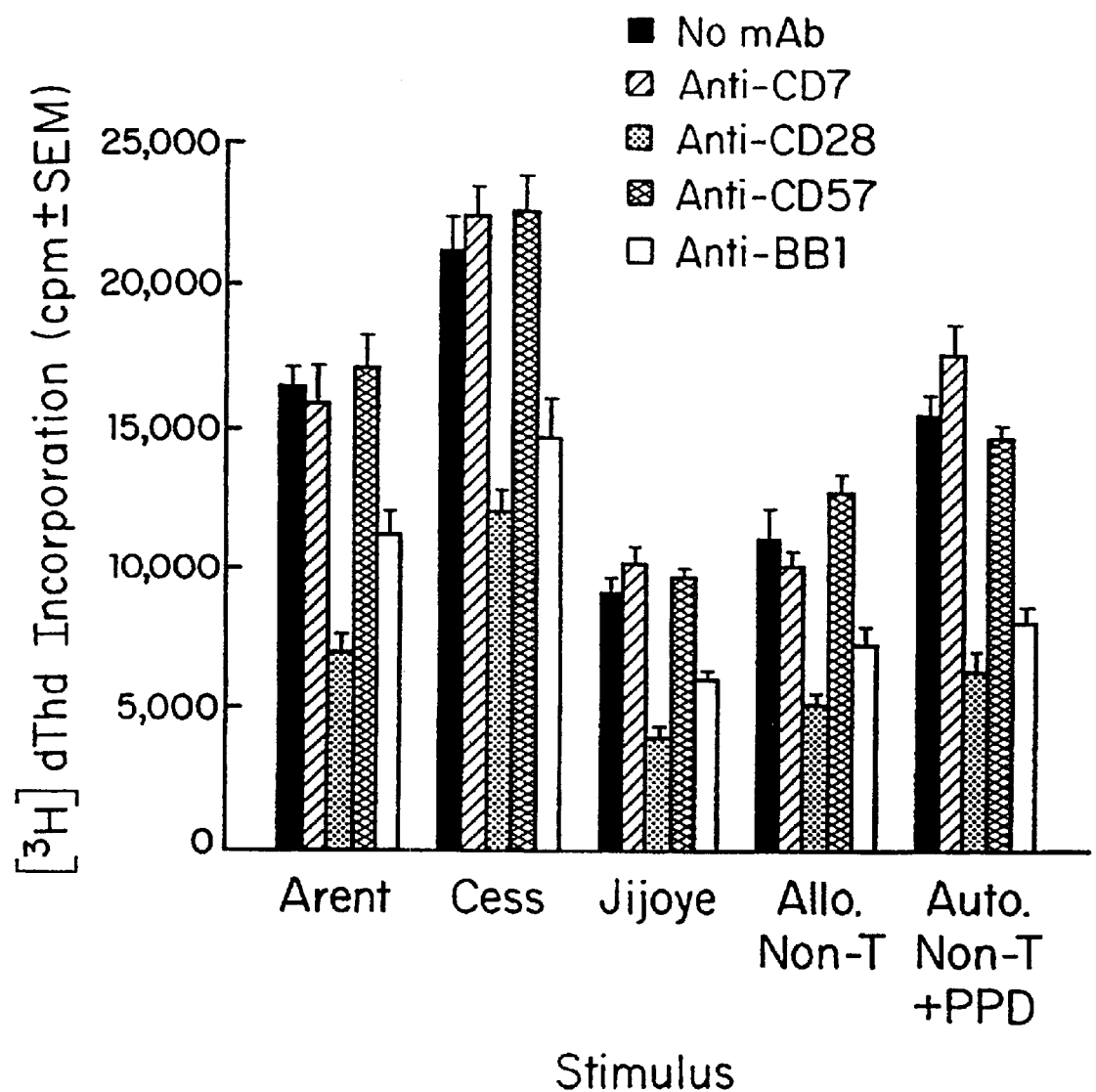
FIG. 6 is a bar graph demonstrating the effect of anti-CD28 and anti-B7 mAbs on T cell proliferation as described in Example 2, infra.

FIG. 6 shows the results of these experiments. The presence of anti-CD28 mAb (9.3 IgG2a) but not that of isotype-matched anti-CD7 mAb (4H9, IgG2a) consistently inhibited the MLR proliferative response of $CD4^+$ T cells to allogeneic B cells. Similarly, the addition of anti-B7 mAb (BB1; IgM) but not that of isotype-matched anti-CD57 HNK1; IgM) to the allogeneic MLR resulted in the inhibition of T cell proliferation. The inhibitory effects of anti-CD28 mAb 9.3 on the MLR responses of T cells are consistent with previous observations reported by Damle et al., *J. Immunol.* 120:1753 (1988) and Damle et al., *Proc. Natl. Acad. Sci. USA* 78:5096 (1981). Similar to the allogeneic MLR, proliferative response of $CD4^+$ T cells to soluble Ag PPD presented by autologous non-T cells was also inhibited by anti-CD28 and anti-B7 mAb. Although both anti-CD28 mAb 9.3 (IgG2a) and anti-B7 mAb, BB1 (IgM) inhibited the allogeneic MLR and the soluble antigen-induced proliferative responses, anti-CD28-mediated inhibition was always stronger than that by anti-B7 for all the responder-stimulator combinations examined. These observations are also consistent with the weaker ability of anti-B7 mAb to block the CD28-mediated adhesion to $B7^+$ B cells as described above.

T Cell-induced Immunoglobulin (Ig) Production by B Cells

To further examine the roles of CD28 and B7 during cognate $T_h$-B interactions, two EBV-transformed B cells lines, IgG-secreting $DR7^+$ CESS and IgM-secreting $DR7^+$ SKW were used. When appropriately stimulated, both these B cells lines significantly increase their production of the respective Ig isotype. First, the effects of DR7-specific $CD4^+$ $CD45RO^+$ $T_h$ line on the Ig production of both CESS and SKW B cells was examined. DR7-primed $CD4^+$ $T_h$ cells were derived from the allogeneic MLC consisting of responder $CD4^+CD45RO^+$ T cells (HLA-A26, A29; B7, B55; DR9, DR10) and irradiated MSAB ($DR7^+$) B cells as stimulator cells as described by Damle et al., *J. Immunol,* 133:1235 (1984), incorporated by reference herein. The isolation of resting $CD4^+CD45RO^+$ T cells and that of DR7-primed $CD4^+$ $CD45RO^+$ T lymphoblasts using discontinuous Percoll density gradient centrifugation was also as described by Damle, supra (1984). These DR7-primed $CD4^+$ $T_h$ cells were continuously propagated in the presence of irradiated MSAB B cells and 50 U/ml of IL-2. Prior to their functional analysis, viable DR7-primed $T_h$ cells were isolated by Ficoll-Hypaque gradient centrifugation and maintained overnight in CM without $DR7^+$ feeder cells or IL-2, after which immunoglobulin secreted in the cell-free supernatant (SN) was quantitated using a solid-phase ELISA.

To examine the effect of $T_h$ cells on Ig production, by both CESS and SKW B cells $2 \times 10^4 - 2.5 \times 10^4$ cells from HLA-$DR7^+$ EBV-transformed B cell lines, IgM-producing SKW or IgG-producing CESS were cultured with varying numbers of DR7-primed $CD4^+CD45RO^+$ $T_h$ cells for 96 h after which cell-free SN from these cultures were collected and assayed for the quantitation of IgM (SKW cultures) or IgG (CESS cultures) using solid-phase ELISA. Exogenous IL-6 (1–100 U/ml) induced Ig production by these B cells was also used as a positive control to monitor the non-cognate Ig production by these B cell lines. Ig production by freshly isolated resting $CD4^+CD45RO^+$ $T_h$ cells (autologous to the DRt-primed $CD4^+$ $T_h$ cells) was also simultaneously examined as a control for DR7-primed $CD4^+$ $T_h$ cells.

Ig Quantitation

IgG or IgM in culture SN were measured using solid-phase ELISA as described by Volkman et al., *Proc. Natl. Acad. Sci. USA* 78:2528 (1981), incorporated by reference herein. Briefly, 96-well flat-bottom microtiter ELISA plates (Corning, Corning N.Y.) were coated with 200 μl/well of sodium carbonate buffer (pH 9.6) containing 10 μg/ml of affinity-purified goat anti-human Ig or IgM Ab (Tago, Burlingame, Calif.) incubated overnight at 4° C., and then washed with PBS and wells were further blocked with 2% BSA in PBS (BSA-PBS). Samples to be assayed were added at appropriate dilution to these wells and incubated with 200 μl/well of 1:1000 dilution of horseradish peroxidase (HRP)-conjugated F(ab')$_2$ fraction of affinity-purified goat anti-human IgG or IgM Ab (Tago). The plates were then washed, and 100 μl/well of o-phenylenediamine (Sigma, St. Louis, Mo.) solution (0.6 mg/ml in citrate-phosphate buffer with pH 5.5 and 0.045% hydrogen peroxide). Color development was stopped with 2N sulfuric acid. Absorbance at 490 nm was measured with an automated ELISA plate reader. Test and control samples were run in triplicate and the values of absorbance were compared to those obtained with known IgG or IgM standards run simultaneously with the SN samples to generate the standard curve using which the concentrations of Ig in culture SN were quantitated. Data are expressed as ng/ml of Ig±SEM of either triplicate or quadruplicate cultures.

Figure 7A:
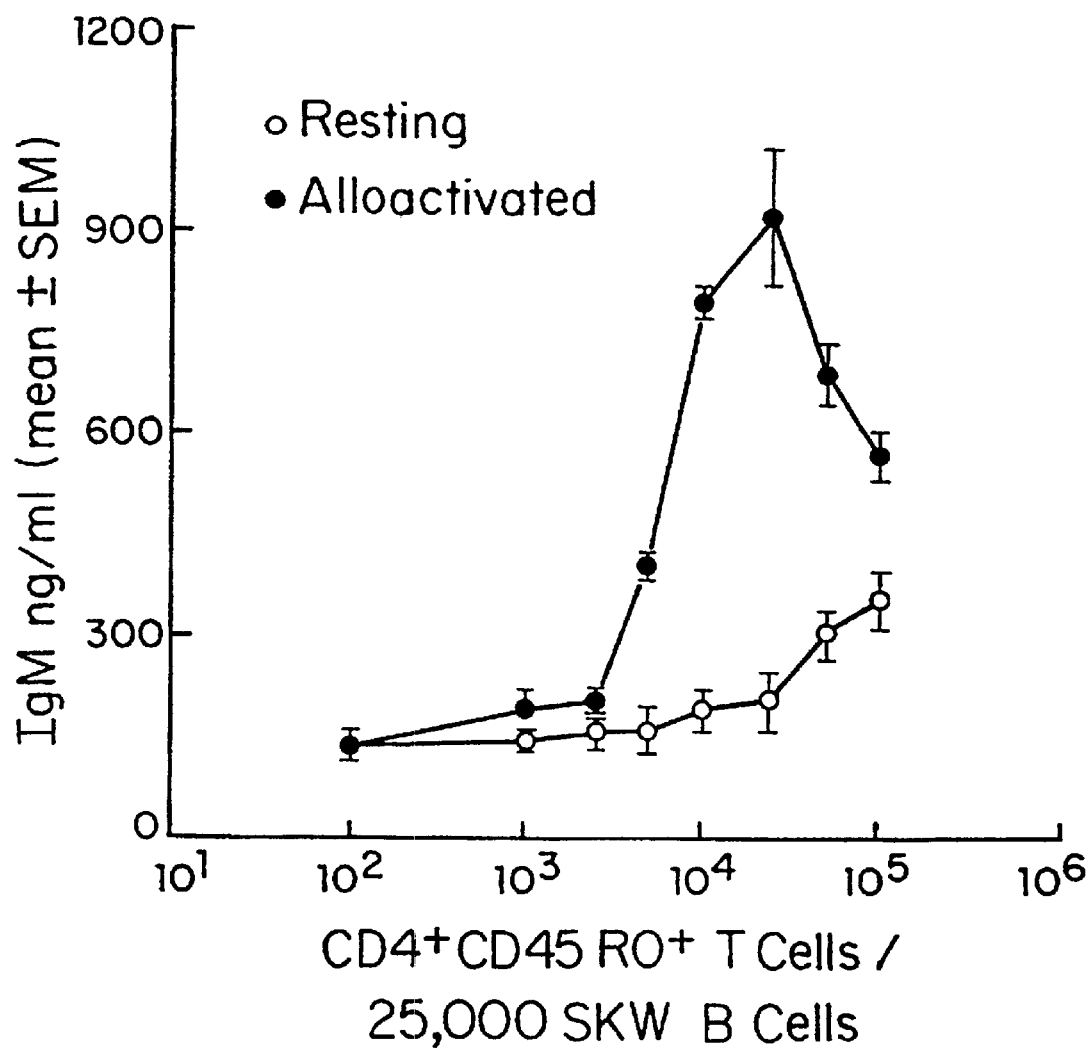
FIG. 7a is a graph showing the effects of DR7-primed CD4$^+$CD45RO$^+$ T$_h$ cells on differentiation of B cells into IgM secreting SKW B cells, as described in Example 2, infra.
Figure 7B:
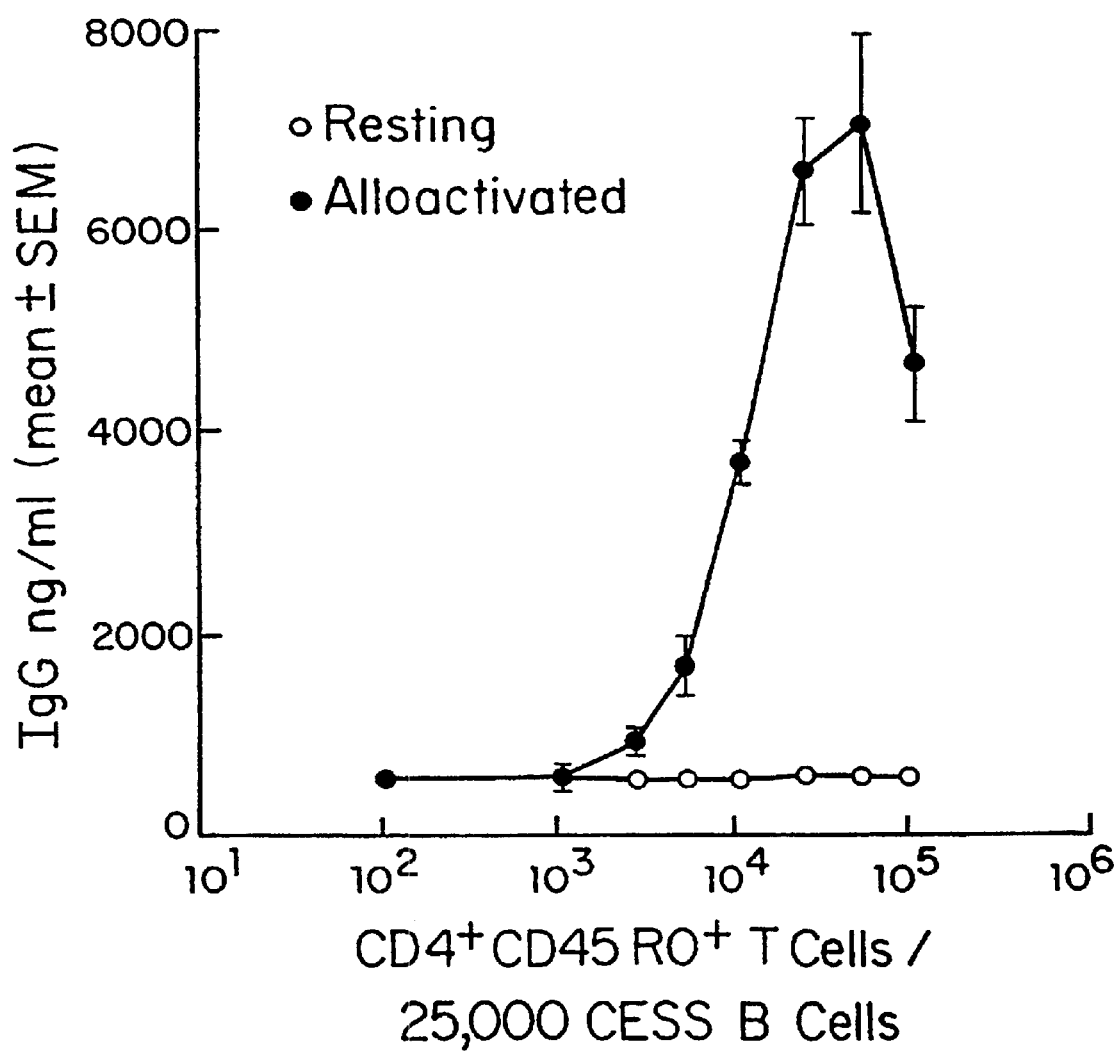
FIG. 7b is a graph showing the effects of DR7-primed CD4$^+$CD45RO$^+$ T$_h$ cells on differentiation of B cells into IgG secreting CESS B cells, as described in Example 2, infra.

FIG. 7 shows the Ig production by either B cell line as a function of the concentration of DR7-primed $T_h$ with optimal Ig production induced at either 1:1 or 1:2 $T_h$:B ratios. At $T_h$:B ratios higher than 1:1 inhibition of Ig production was observed. Hence, all further experiments were carried out using a $T_h$:B ratio of 1:2. As shown in FIG. 7, these unprimed resting CD4$^+$ $T_h$ cells slightly induced IgM production by SKW B cells but has no effect on the IgG production by CESS B cells in 4-day cultures. This slight helper effect observed with unprimed CD4$^+$CD45RO$^+$ population during the Ig induction cultures. The production of Ig by CESS (IgG) or SKW (IgM) B cells induced by DR7-primed CD4$^+$ $T_h$ was specific for HLA-DR7 because similarly activated DRw6-primed CD4$^+$ $T_h$ (stimulated with DRw6$^+$ ARENT B cells and autologous to the DR7-primed $T_h$) were unable to induce Ig production by either CESS or SKW B cells.

Figure 8A:
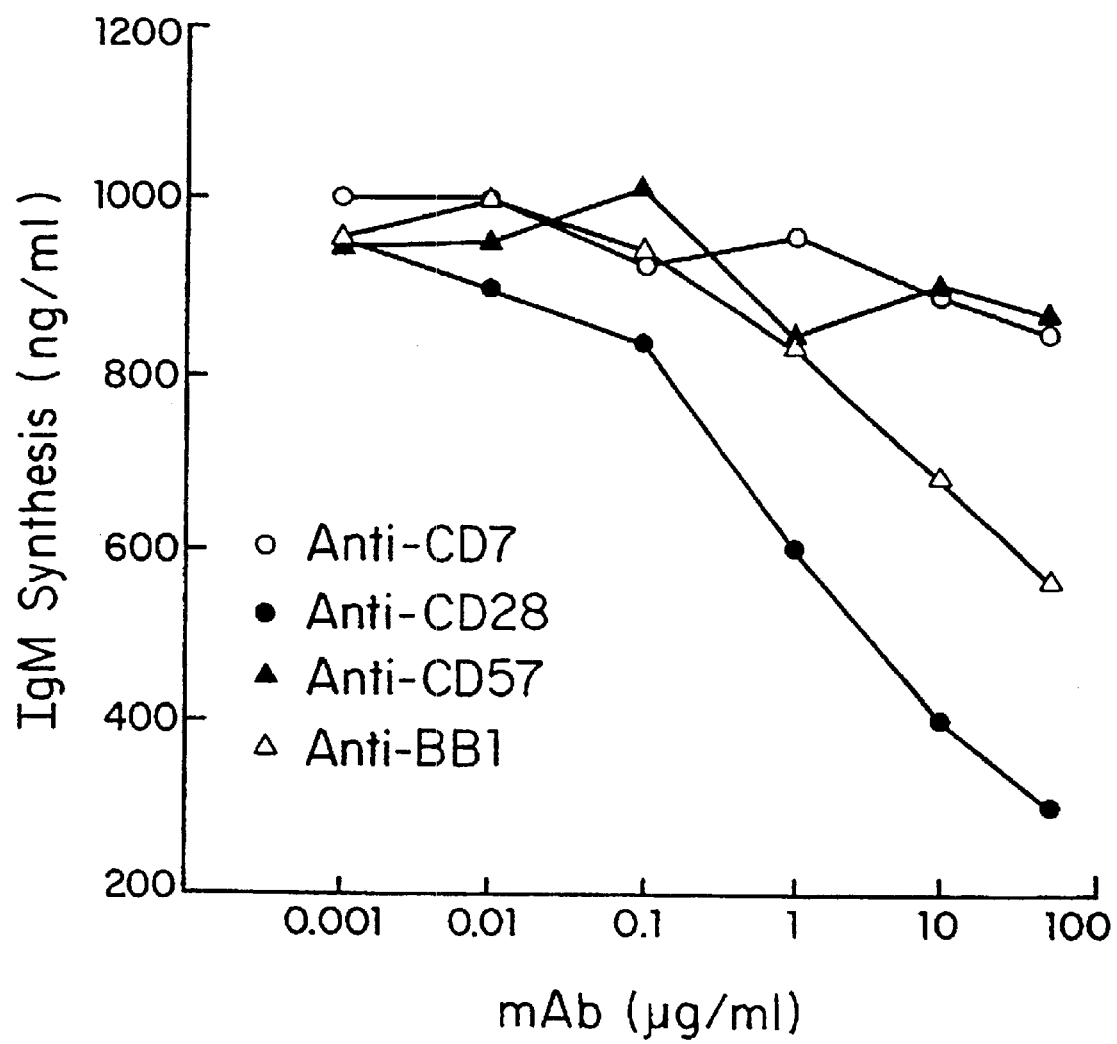
FIG. 8a is a graph showing the effect of anti-CD28 and anti-B7 mAbs on the T$_h$-induced production of IgM by B cells as described in Example 2, infra.
Figure 8B:
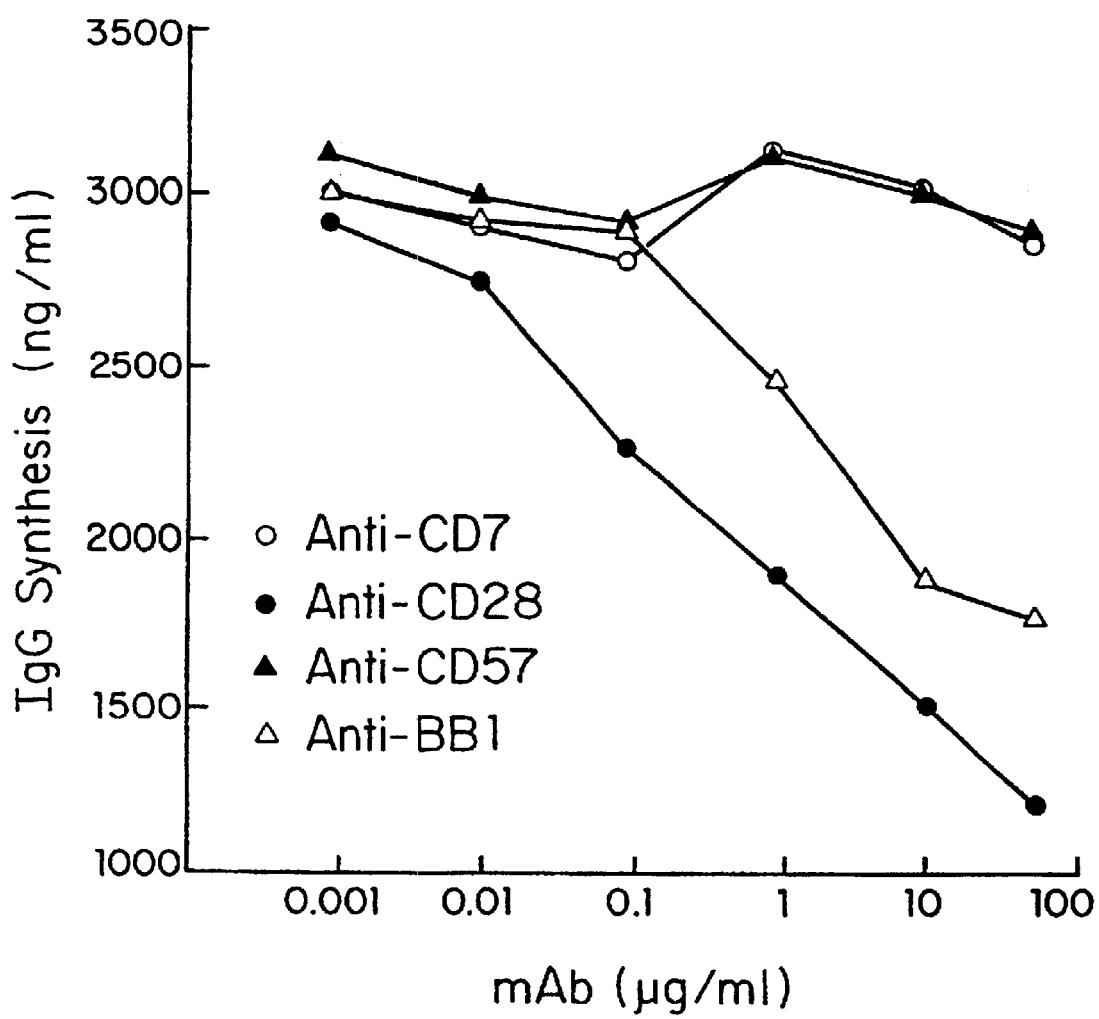
FIG. 8b is a graph showing the effect of anti-CD28 and anti-B7 mAbs on the T$_h$-induced production of IgG by B cells as described in Example 2, infra.

The roles of CD28 and B7 during cognate $T_h$:B-induced Ig production were further examined using anti-CD28 and anti-B7 mAbs. Both CESS and SKW B cells constitutively express B7 antigen on their surface and thus, represent a source of uniformly activated B cell populations for use in $T_h$-B cognate interactions or in cytokine-driven non-cognate maturation. Thus, DR7$^+$ B cells (CESS or SKW) were cultured for 4 days with DR7-specific CD4$^+$ $T_h$ line at $T_h$:B ratio of 1:2 and mAb to CD28 and B7, (and CD7 and CD57 as controls) were added to these cultures at different concentrations. Ig production (IgM, FIG. 8a and IgG, FIG. 8b) at the end of 3-day cultures was quantitated in cell-free SN. FIG. 8 shows that both anti-CD28 and anti-B7 mAbs but not their isotype-matched mAb controls (anti-CD7 and anti-CD57, respectively) inhibited $T_h$ induced Ig production by B cells in a does-dependent manner. Once again, anti-CD28 mAb-mediated inhibition of Ig production was stronger than that by anti-B7 mAb. In contrast, Ig production by either B cells induced by exogenous IL-6 (non-cognate differentiation) was not affected by any of the above mAb.

These results strongly suggest that the interaction between CD28 and B7, during cognate $T_h$-B collaboration, in addition to activation of $T_h$ cells, is pivotal to the differentiation of activated B cells into Ig secreting cells.

The above results demonstrate the relationship of CD28 receptor and its ligand, the B7 antigen, as a co-stimulatory transmembrane receptor-ligand pair influencing $T_h$:B interactions. Involvement of both CD28 and B7 during $T_h$:B collaboration was demonstrated by inhibition by anti-CD28 and anti-B7 of not only $T_h$ cell activation but also $T_h$-induced differentiation of B cells into IgSC. It appears as if the observed inhibitory effects of anti-CD28 and anti-B7 mAbs are due to the inhibition of CD28:B7 interaction underlying these responses.

Interaction between CD28 receptor and B7 antigen may influence the production of cytokines and thus B cell differentiation. Ligation of CD28 by B7 during $T_h$:B collaboration may facilitate sustained synthesis and delivery of cytokines for their utilization during the differentiation of B cells into immunoglobulin secreting cells. The lack of inhibition by anti-CD28 and anti-B7 mAbs of cell dependent differentiation of CESS or SKW B cells induced with exogenous IL-4 or IL-6 suggests that CD28:B7 interaction controls either production of these cytokines, or their targeted delivery to B cells, or both of these events.

The interaction of CD28 and B7 is most likely not restricted to $T_h$:B cell interactions, and applies more generally to other antigen-presenting cells such as monocyte/Mφ, dendritic cells, and epidermal Langerhans cells. Ligation of a nominal antigen presented in conjunction with MHC class II molecules on the surface of antigen-presenting cells by the TcR/CD3 complex on the surface of $T_h$ cells may lead to elevated expression of B7 antigen by these cells, which, via the interaction with CD28, then facilitates the production of various cytokines by $T_h$. This in turn drives both growth and differentiation of both $T_h$ and B cells.

EXAMPLE 3

Characterization of the Interaction between CD28 Receptor and B7 Antigen

I. Preparation of Fusion Proteins

To further characterize the biochemical and functional aspects of the interactions between the CD28 receptor and B7 antigen, fusion proteins of B7 and CD28 with human immunoglobulin C gamma 1 (human Ig Cγ1) chains were constructed and expressed and used to measure the specificity and apparent affinity of interaction between these molecules. Purified B7Ig fusion protein, and CHO cells transfected with B7 antigen were used to investigate the functional effects of this interaction on T cell activation and cytokine production.

Preparation of B7Ig and CD28Ig Fusion Proteins

B7Ig and CD28Ig fusion proteins were prepared as follows. DNA encoding the amino acid sequence corresponding to the extracellular domain of the respective protein (B7 and CD28) was joined to DNA encoding the amino acid sequences corresponding to the hinge, CH2 and CH3 regions of human immunoglobulin Cγ1. This was accomplished as follows.

Plasmid Construction

Expression plasmids were used containing cDNA encoding the amino acid sequence corresponding to CD28 (pCD28) as described by Aruffo and Seed, *Proc. Natl. Acad. Sci. USA* 84:8573 (1987), incorporated by reference, and provided by Drs. Aruffo and Seed, Mass General Hospital, Boston, Mass. Expression plasmids containing cDNA encoding the amino acid sequence corresponding to CD5 (pCD5) as described by Aruffo, *Cell* 61:1303 (1990), and also provided by Dr. Aruffo, and cDNA encoding the amino acid sequence corresponding to B7 (pB7) as described by Freeman et al., *J. Immunol.* 143:2714 (1989)) and provided by Dr. Freeman, Dana Farber Cancer Institute, Boston, Mass., were also used.

For initial attempts at expression of soluble forms of CD28 and B7, constructs were made (OMCD28 and OMB7) in which stop codons were introduced upstream of the transmembrane domains and the native signal peptides were replaced with the signal peptide from oncostatin M (Malik et al., *Mol. Cell Biol.* 9:2847 (1989)). These were made using synthetic oligonucleotides for reconstruction (OMCD28) or as primers (OMB7) for PCR. OMCD28, is a CD28 cDNA modified for more efficient expression by replacing the signal peptide with the analogous region from oncostatin M. CD28Ig and B7Ig fusion constructs were made in two parts. The 5' portions were made using OMCD28 and OMB7 as templates and the oligonucleotide, CTAGCCACTGAAGCTTCACCATGGGTGTACTGCTCACAC (SEQ ID NO:1) (corresponding to the oncostatin M signal peptide) as a forward primer, and either TGGCATGGGCTCCTGATCAGGCTTAGAAGGTCCGGGAAA (SEQ ID NO:2), or, TTTGGGCTCCTGATCAGGAAAATGCTCTTGCTTGGTTGT (SEQ ID NO:3) as reverse primers, respectively. Products of the PCR reactions were cleaved with restriction endonucleases (Hind III and BclI) as sites introduced in the PCR primers and gel purified.

The 3' portion of the fusion constructs corresponding to human Ig Cγ1 sequences was made by a coupled reverse transcriptase (from Avian myeloblastosis virus; Life Sciences Associates, Bayport, N.Y.)-PCR reaction using RNA from a myeloma cell line producing human-mouse chimeric mAb L6 (provided by Dr. P. Fell and M. Gayle, Bristol-Myers Squibb Pharmaceutical Research Institute, Seattle, Wash.) as template. The oligonucleotide, AAGCAAGAGCATTTTCCTGATCAGGAGCCCAAATCTTCTGACAAAACTCACACATCCCCAC-CGTCCCCAGCACCTGAACTCCTG (SEQ ID NO:4), was used as forward primer, and CTTCGACCAGTCTAGAAGCATCCTCGTGCGACCGCGAGAGC (SEQ ID NO:5) as reverse primer. Reaction products were cleaved with BclI and XbaI and gel purified. Final constructs were assembled by ligating HindIII/BclI cleaved fragments containing CD28 or B7 sequences together with BclI/XbaI cleaved fragment containing Ig Cγ1 sequences into HindIII/XbaI cleaved CDM8. Ligation products were transformed into MC1061/p3 E. coli cells and colonies were screened for the appropriate plasmids. Sequences of the resulting constructs were confirmed by DNA sequencing. The DNA used in the B7 construct encodes amino acids from about position 1 to about position 215 of the sequence corresponding to the extracellular domain of the B7 antigen, and for CD28, the DNA encoding amino acids from about position 1 to about position 134 of the sequence corresponding to the extracellular domain of the CD28 receptor.

CD5Ig was constructed in identical fashion, using CATTGCACAGTCAAGCTTCCATGCCCATGGGTTCTCTGGCCACCTTG (SEQ ID NO:6), as forward primer and ATCCACAGTGCAGTGATCATTTGGATCCTGGCATGTGAC (SEQ ID NO:7) as reverse primer. The PCR product was restriction endonuclease digested and ligated with the Ig Cγ1 fragment as described above. The resulting construct (CD5Ig) encodes an amino acid sequence containing residues from about position 1 to about position 347 of CD5, two amino acids introduced by the construction procedure (amino acids DQ), followed by the Ig Cγ1 hinge region.

In initial attempts to make soluble derivatives of B7 and CD28, cDNA constructs were made encoding molecules truncated at the $NH_2$-terminal side of their transmembrane domains. In both cases, the native signal peptides were replaced with the signal peptide from oncostatin M (Malik, supra, 1989), which mediates efficient release of secreted proteins in transient expression assays. The cDNAs were cloned into an expression vector, transfected into COS cells, and spent culture medium was tested for secreted forms of B7 and CD28. In this fashion, several soluble forms of B7 were produced, but in repeated attempts, soluble CD28 molecules were not detected.

Figure 9:
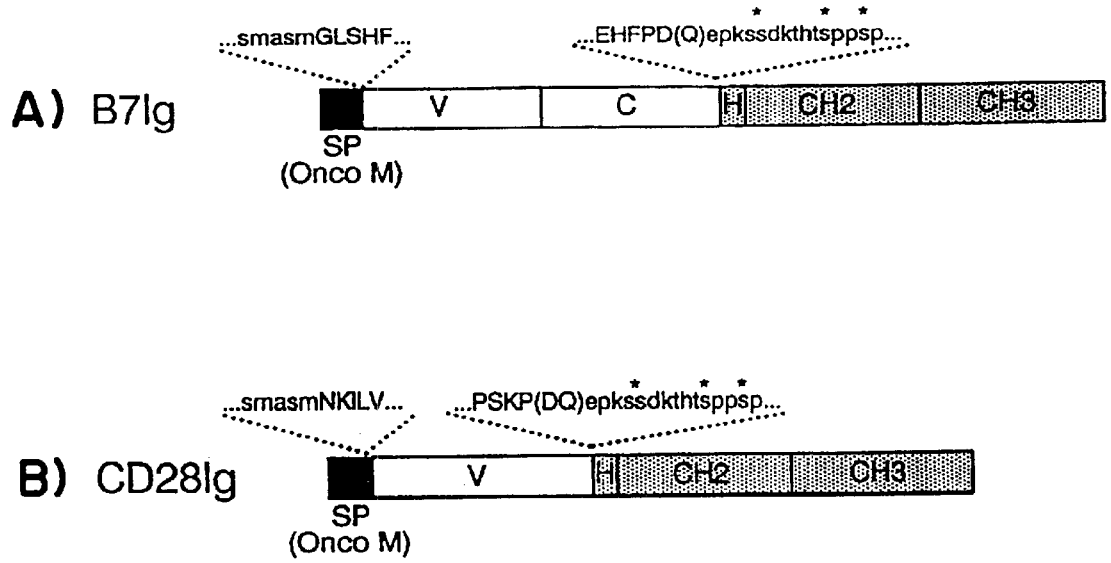
FIG. 9a is a diagrammatic representation of B7Ig protein fusion constructs as described in Example 3, infra (dark shaded regions=oncostatin M; unshaded regions=B7, stippled regions=human Ig Cγ1).
FIG. 9b is a diagrammatic representation of CD28Ig protein fusion constructs as described in Example 3, infra (dark shaded regions=oncostatin M; unshaded regions=CD28, stippled regions=human Ig Cγ1).

The next step was to construct receptor Ig Cγ1 fusion proteins. The DNAs encoding amino acid sequences corresponding to B7 and CD28 extracellular regions, preceded by the signal peptide to oncostatin M, were fused in frame to an Ig Cγ1 cDNA, as shown in FIG. 9. During construction, the Ig hinge disulfides were mutated to serine residues to abolish intrachain disulfide bonding. The resulting fusion proteins were produced in COS cells and purified by affinity chromatography on immobilized protein A as described below. Yields of purified protein were typically 1.5–4.5 mg/liter of spent culture medium.

Polymerase Chain Reaction (PCR)

For PCR, DNA fragments were amplified using primer pairs as described below for each fusion protein. PCR reactions (0.1 ml final volume) were run in Tag polymerase buffer (Stratagene, La Jolla, Calif.), containing 20 μmoles each of dNTP; 50–100 pmoles of the indicated primers; template (1 ng plasmid or cDNA synthesized from $\leq 1$ μg total RNA using random hexamer primer, as described by Kawasaki in PCR Protocols, Academic Press, pp. 21–27 (1990), incorporated by reference herein); and Tag polymerase (Stratagene). Reactions were run on a thermocycler (Perkin Elmer Corp., Norwalk, Conn.) for 16–30 cycles (a typical cycle consisted of steps of 1 min at 94° C., 1–2 min at 50° C. and 1–3 min at 72° C.).

Cell Culture and Transfections

COS (monkey kidney cells) were transfected with expression plasmids using a modification of the protocol of Seed and Aruffo (*Proc. Natl. Acad. Sci.* 84:3365 (1987)), incorporated by reference herein. Cells were seeded at $10^6$ per 10 cm diameter culture dish 18–24 h before transfection. Plasmid DNA was added (approximately 15 μg/dish) in a volume of 5 ml of serum-free DMEM containing 0.1 mM cloroquine and 600 μg/ml DEAE Dextran, and cells were incubated for 3–3.5 h at 37° C. Transfected cells were then briefly treated (approximately 2 min) with 10% dimethyl sulfoxide in PBS and incubated at 37° C. for 16–24 h in DMEM containing 10% FCS. At 24 h after transfection, culture medium was removed and replaced with serum-free DMEM (6 ml/dish). Incubation was continued for 3 days at 37° C., at which time the spent medium was collected and fresh serum-free medium was added. After an additional 3 days at 37° C., the spent medium was again collected and cells were discarded.

CHO cells expressing CD28, CD5 or B7 were isolated as described by Linsley et al., (1991) supra, as follows: Briefly, stable transfectants expressing CD28, CD5, or B7, were isolated following cotransfection of dihydrofolate reductase-deficient Chinese hamster ovary (dhfr⁻ CHO) cells with a mixture of the appropriate expression plasmid and the selectable marker, pSV2dhfr, as described above in Example 1. Transfectants were then grown in increasing concentrations of methotrexate to a final level of 1 μM and were maintained in DMEM supplemented with 10% fetal bovine serum (FBS), 0.2 mM proline and 1 μM methotrexate. CHO lines expressing high levels of CD28 (CD28⁺ CHO) or B7 (B7⁺ CHO) were isolated by multiple rounds of fluorescence-activated cell sorting ($FACS^R$) following indirect immunostaining with mAbs 9.3 or BB-1. Amplified CHO cells negative for surface expression of CD28 or B7 (dhfr⁺ CHO) were also isolated by $FACS^R$ from CD28-transfected populations.

Immunostaining and $FACS^R$ Analysis

Transfected CHO cells or activated T cells were analyzed by indirect immunostaining. Before staining, CHO cells were removed from their culture vessels by incubation in PBS containing 10 mM EDTA. Cells were first incubated with murine mAbs 9.3 (Hansen et al., *Immunogenetics* 10:247 (1980)) or BB-1 (Yokochi et al., supra) at 10 μg/ml, or with Ig fusion proteins (CD28Ig, B7Ig, CD5Ig or chimeric mAb L6 containing Ig Cγ1, all at 10 μg/ml in DMEM containing 10% FCS) for 1–2 h at 4° C. Cells were then washed, and incubated for an additional 0.5–2 h at 4° C. with a FITC-conjugated second step reagent (goat anti-mouse Ig serum for murine mAbs, or goat anti-human Ig Cγ serum for fusion proteins (Tago, Inc., Burlingame, Calif.). Fluorescence was analyzed on 10,000 stained cells using a FACS IV$^R$ cell sorter (Becton Dickinson and Co., Mountain View, Calif.) equipped with a four decade logarithmic amplifier.

Purification of Ig Fusion Proteins

The first, second and third collections of spent serum-free culture media from transfected COS cells were used as sources for the purification of Ig fusion proteins. After removal of cellular debris by low speed centrifugation, medium was applied to a column (approximately 200–400 ml medium/ml packed bed volume) of immobilized protein A (Repligen Corp., Cambridge, Mass.) equilibrated with 0.05 M sodium citrate, pH 8.0. After application of the medium, the column was washed with 1 M potassium phosphate, pH 8, and bound protein was eluted with 0.05 M sodium citrate, pH 3. Fractions were collected and immediately neutralized by addition of ⅒ volume of 2 M Tris, pH 8. Fractions containing the peak of $A_{280}$ absorbing material were pooled and dialyzed against PBS before use. Extinction coefficients of 2.4 and 2.8 ml/mg for CD28Ig and B7Ig, respectively, by amino acid analysis of solutions of known absorbance. The recovery of purified CD28Ig and B7Ig binding activities were nearly quantitative as judged by FACS$^R$ analysis after indirect fluorescent staining of B7$^+$ and CD28$^+$ CHO cells.

SDS Page

Figure 10:
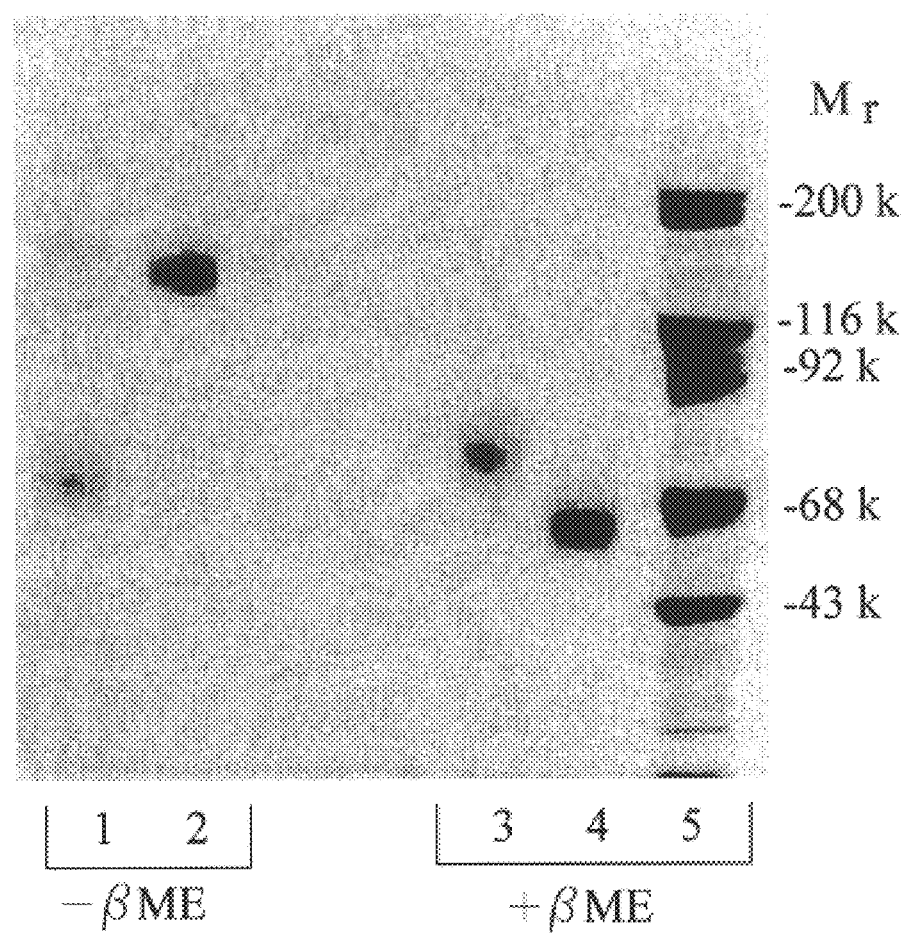
FIG. 10 is a photograph of a gel obtained from purification of B7Ig and CD28 protein fusion constructs as described in Example 3, infra.

SDS-PAGE was performed on linear acrylamide gradients gels with stacking gels of acrylamide. Aliquots (1 μg) of B7Ig (lanes 1 and 3 of FIG. 10) or CD28Ig (lanes 2 and 4) were subjected to SDS-PAGE (4–12% acrylamide gradient) under nonreducing (–βME, lanes 1 and 2) or reducing (+βME, lanes 3 and 4) conditions. Lane 5 of FIG. 10 shows molecular weight ($M_r$) markers. Gels were stained with Coomassie Brilliant Blue, destained, and photographed or dried and exposed to X-ray film (Kodak XAR-5; Eastman Kodak Co., Rochester, N.Y.) for autoradiography to visualize proteins.

As shown in FIG. 10, the B7Ig fusion protein migrated during SDS-PAGE under nonreducing conditions predominantly as a single species of $M_r$ 70,000, with a small amount of material migrating as a $M_r$ approximately 150,000 species. After reduction, a single $M_r$ approximately 75,000 species was observed. CD28Ig migrated as a Mr approximately 140,000 species under non-reducing conditions and a $M_r$ approximately 70,000 species after reduction, indicating that it was expressed as a homodimer. Since the Ig Cγ1 hinge cysteines had been mutated, disulfide linkage probably involved cysteine residues which naturally form interchain bonds in the CD28 homodimer (Hansen et al., *Immunogenetics* 10:247 (1980)).

DNAs encoding the amino acid sequences corresponding to the B7Ig fusion protein and CD28Ig fusion protein have been deposited with the ATCC in Rockville, Md., under the terms of the Budapest Treaty on May 31, 1991 and there have been accorded accession numbers: 68627 (B7Ig) and 68628 (CD28Ig).

II. Characterization of B7Ig and CD28Ig Cγ1 Fusion Proteins

Figure 11:
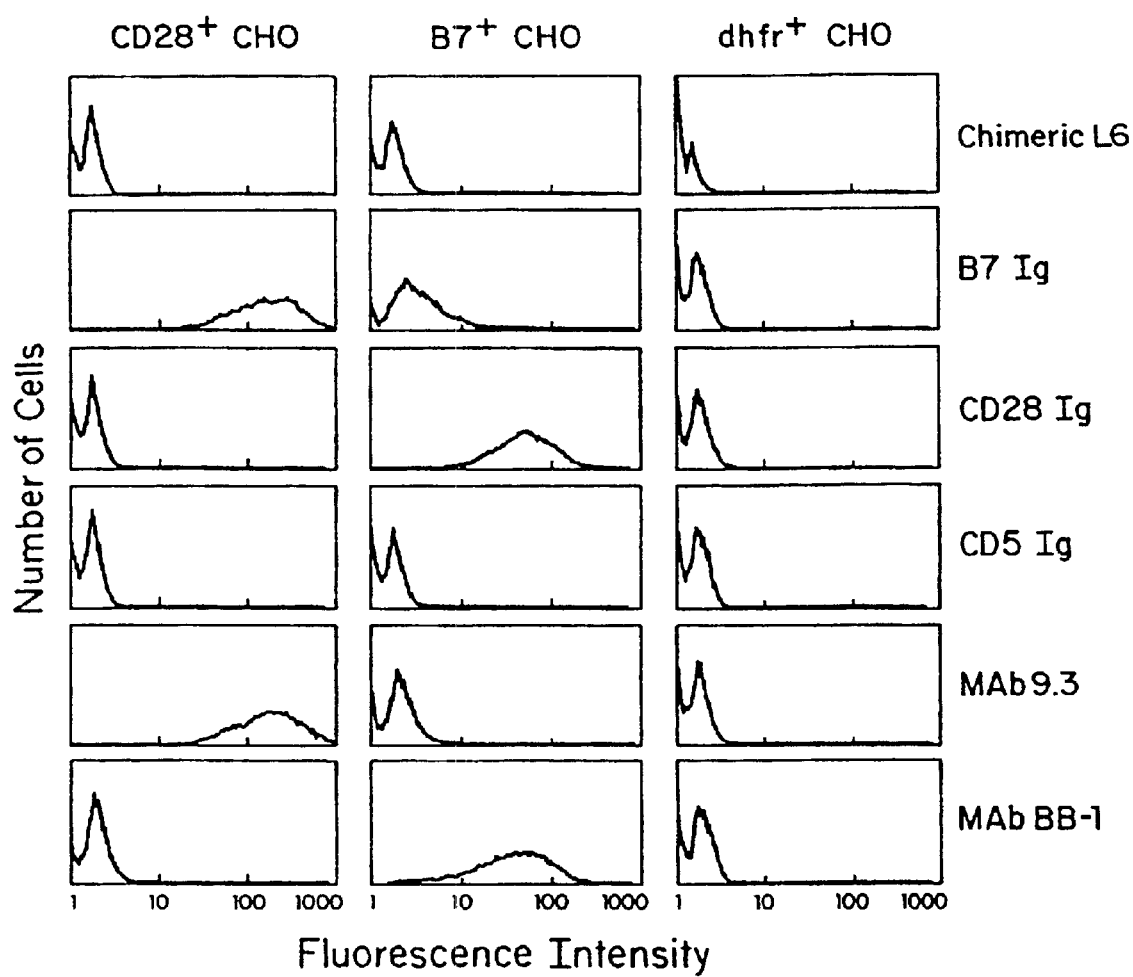
FIG. 11 depicts the results of FACS$^R$ analysis of binding of the B7Ig and CD28Ig fusion proteins to transfected CHO cells as described in Example 3, infra.

To investigate the functional activities of B7Ig and CD28Ig, binding of CHO cell lines expressing CD28 or B7 was tested as follows. In early experiments, spent culture media from transfected COS cells was used as a source of fusion protein, while in later experiments, purified proteins were used (see FIG. 11).

Binding of B7Ig and CD28Ig to CHO Cells

Binding of CD28Ig and B7Ig fusion proteins was detected by addition of FITC-conjugated goat anti-human Ig second step reagent as described above. B7Ig was bound by CD28$^+$ CHO, while CD28Ig was bound by B7$^+$ CHO. B7Ig also bound weakly to B7$^+$ CHO (FIG. 11), suggesting that this molecule has a tendency to form homophilic interactions. No binding was detected of chimeric mAb L6 containing human Ig Cγ1, or another fusion protein, CD5Ig. Thus B7Ig and CD28Ig retain binding activity for their respective counter-receptors.

The apparent affinity of interaction between B7 and CD28 was next determined. B7Ig was either iodinated or metabolically labeled with [$^{35}$S]methionine, and radiolabeled derivatives were tested for binding to immobilized CD28Ig or to CD28$^+$ CHO cells.

Radiolabeling of B7Ig

Purified B7Ig (25 μg) in a volume of 0.25 ml of 0.12 M sodium phosphate, pH 6.8 was iodinated using 2 mCi $^{125}$I and 10 μg of chloramin T. After 5 min at 23° C., the reaction was stopped by the addition of 20 μg sodium metabisulfite, followed by 3 mg of KI and 1 mg of BSA. Iodinated protein was separated from untreated $^{125}$I by chromatography on a 5-ml column of Sephadex G-10 equilibrated with PBS containing 10% FCS. Peak fractions were collected and pooled. The specific activity of $^{125}$I-B7Ig labeled in this fashion was 1.5×10$^6$ cpm/pmol.

B7Ig was also metabolically labeled with [$^{35}$S] methionine. COS cells were transfected with a plasmid encoding B7Ig as described above. At 24 h after transfection, [$^{35}$S]methionine (<800 Ci/mmol; Amersham Corp., Arlington Heights, Ill.) was added to concentrations of 115 μCi/ml) in DMEM containing 10% FCS and 10% normal levels of methionine. After incubation at 37° C. for 3 d, medium was collected and used for purification of B7Ig as described above. Concentrations of [$^{35}$S]methionine-labeled B7Ig were estimated by comparison of staining intensity after SDS-PAGE with intensities of known amounts of unlabeled B7Ig. The specific activity of [$^{35}$S] methionine-labeled B7Ig was approximately 2×10$^6$ cpm/μg.

Binding Assays

Figure 12:
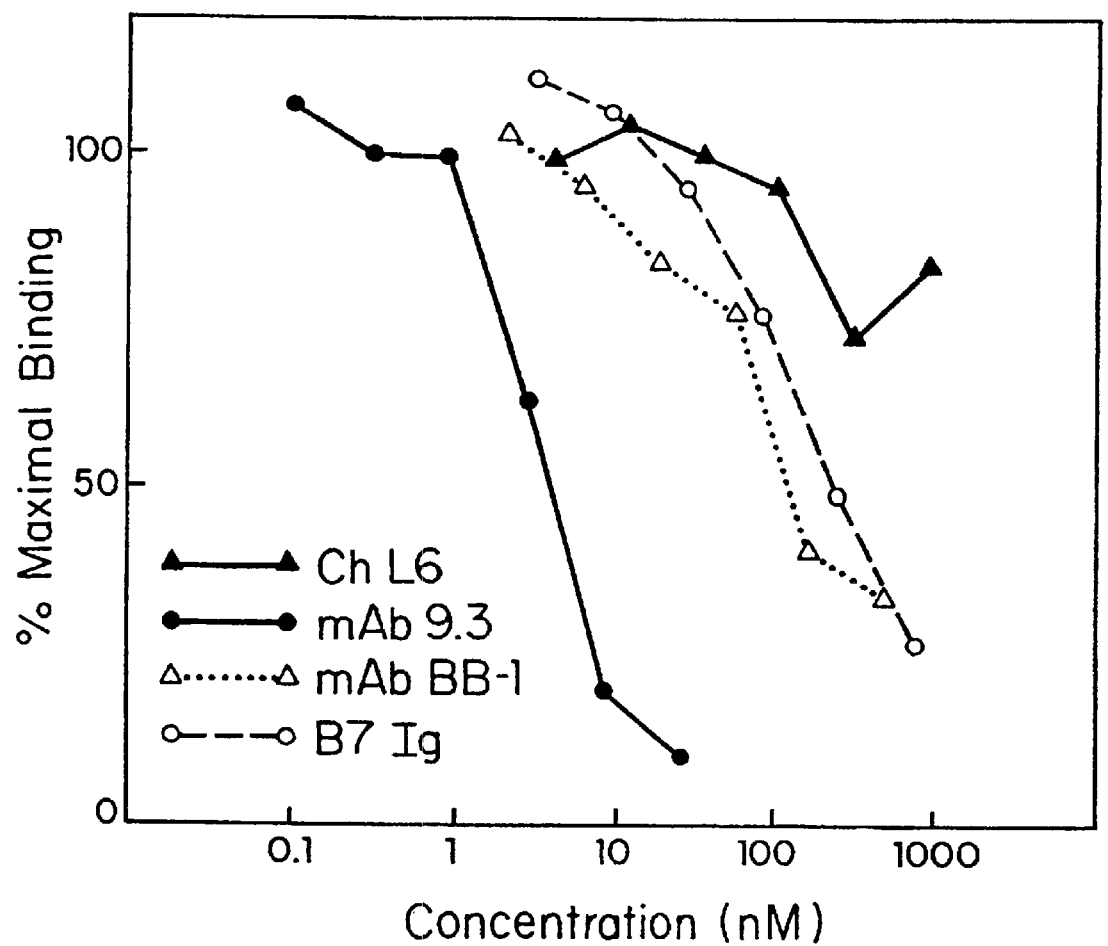
FIG. 12 is a graph illustrating competition binding analysis of $^{125}$I-labeled B7Ig fusion protein to immobilized CD28Ig fusion protein as described in Example 3, infra.

For assays using immobilized CD28Ig, 96-well plastic dishes were coated for 16–24 h with a solution containing CD28Ig (0.5 μg in a volume of 0.05 ml of 10 mM Tris, pH 8). Wells were then blocked with binding buffer (DMEM containing 50 mM BES, pH 6.8, 0.1% BSA, and 10% FCS) (Sigma Chemical Co., St. Louis, Mo.) before addition of a solution (0.09 ml) containing $^{125}$I-B7Ig (approximately 3×10$^6$ cpm, 2×10$^6$ cpm/pmol) or [$^{35}$S]-B7Ig (1.5×10$^5$ cpm) in the presence or absence of competitor to a concentration of 24 nM in the presence of the concentrations of unlabeled chimeric L6 mAb, mAb 9.3, mAb BB-1 or B7Ig, as indicated in FIG. 12. After incubation for 2–3 h at 23° C., wells were washed once with binding buffer, and four times with PBS. Plate-bound radioactivity was then solubilized by addition of 0.5 N NaOH, and quantified by liquid scintillation or gamma counting. In FIG. 12, radioactivity is expressed as a percentage of radioactivity bound to wells treated without competitor (7,800 cpm). Each point represents the mean of duplicate determinations; replicates generally varied from the mean by ≦20%. Concentrations were calculated based on a $M_r$ of 75,000 per binding site for mAbs and 51,000 per binding site for B7Ig. When binding of $^{125}$I-B7 to CD28$^+$ CHO cells was measured, cells were seeded (2.5×10$^4$/well) in 96-well plates 16–24 h before the start of the experiment. Binding was otherwise measured as described above.

The results of a competition binding experiment using $^{125}$I-B7Ig and immobilized CD28Ig are shown in FIG. 12. Binding of $^{125}$I-B7Ig was competed in dose-dependent fashion by unlabeled B7Ig, and by mAbs 9.3 and BB-1. mAb 9.3 was the most effective competitor (half-maximal inhibition at 4.3 nM), followed by mAb BB-1 (half-maximal inhibition at 140 nM) and B7 Ig (half-maximal inhibition at 280 nM). Thus, mAb 9.3 was approximately 65-fold more effective as a competitor than B7Ig, indicating that the mAb has greater apparent affinity for CD28. The same relative difference in avidities was seen when [$^{35}$S]methionine-labeled B7Ig was used. Chimeric mAb L6 did not significantly inhibit binding. The inhibition at high concentrations in FIG. 12 was not seen in other experiments.

When the competition data shown in FIG. 12 were replotted in the Scatchard representation (FIG. 13), a single class of binding sites was observed (binding constant ($K_d$) estimated from the slope of the line best fitting the experimental data (r=−0.985), $K_d$ of approximately 200 nM. An identical $K_d$ was detected for binding of $^{125}$-B7Ig to CD28$^+$ CHO cells. Thus, both membrane bound CD28 and immobilized CD28Ig showed similar apparent affinities for $^{125}$I-B7.

Binding of B7Ig to CD28 Expressed on T Cells

Although B7Ig bound to immobilized CD28Ig, and to CD28$^+$ CHO cells, it was not known, whether B7Ig could bind to CD28 naturally expressed on T cells. This is an important consideration since the level of CD28 on transfected cells was approximately 10-fold higher than that found on PHA-activated T cells as shown above in Example 1. PHA-activated T cells were prepared as follows.

Cell Separation and Stimulation

PBL were isolated by centrifugation through Lymphocyte Separation Medium (Litton Bionetics, Kensington, Md.) and cultured in 96-well, flat-bottomed plates (4×10$^4$ cells/well, in a volume of 0.2 ml) in RPMI containing 10% FCS. Cellular proliferation of quadruplicate cultures was measured by uptake of [$^3$H]thymidine during the last 5 h of a 3 day (d) culture. PHA-activated T cells were prepared by culturing PBL with 1 μg/ml PHA (Wellcome) for 5 d, and 1 d in medium lacking PHA. Viable cells were collected by sedimentation through Lymphocyte Separation Medium before use.

PHA-activated T cells were then tested for binding of B7Ig (10 μg/ml) by FACS$^R$ analysis after indirect immunofluorescence as described above. Where indicated (FIG. 14), mAbs 9.3 or BB-1 were also added at 10 μg/ml to cells simultaneously with B7Ig. Bound mAb was detected with a FITC-conjugated goat anti-human Ig Cγ1 reagent.

Figure 14:
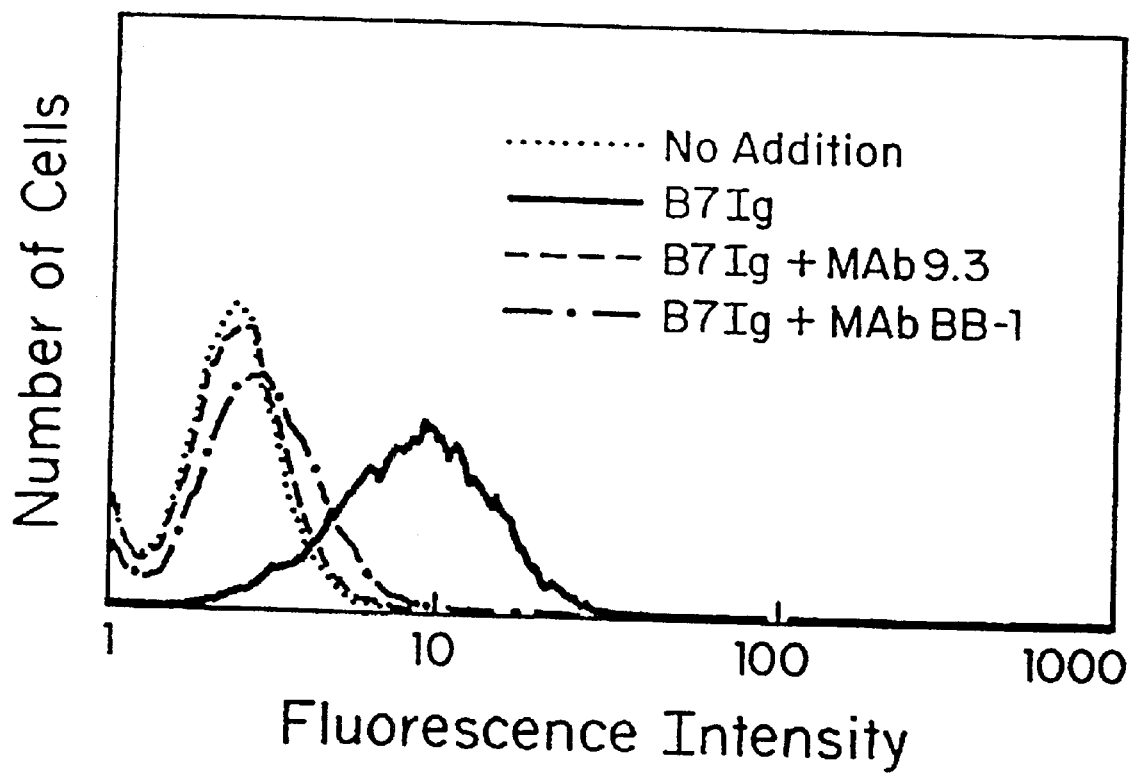
FIG. 14 is a graph of FACS$^R$ profiles of B7Ig fusion protein binding to PHA blasts as described in Example 3, infra.

As shown in FIG. 14, these cells bound significant levels of B7Ig, and binding was inhibited by mAbs 9.3 and BB-1.

The identity of B7Ig-binding proteins was also determined by immunoprecipitation analysis of $^{125}$I-surface labeled cells as follows.

Cell Surface Iodination and Immunoprecipitation

PHA-activated T cells were cell-surface labeled with $^{125}$I using lactoperoxidase and $H_2O_2$ as described by Vitetta et al., *J. Exp. Med.* 134:242 (1971), incorporated by reference herein. Aliquots of a nonionic detergent extract of labeled cells (approximately 3×10$^8$ cpm in a volume of 0.12 ml) were prepared as described by Linsley et al., *J. Biol. Chem.* 263: 8390 (1988), incorporated by reference herein, and subjected to immunoprecipitation analysis and SDS-PAGE, as described above using a 5–15% acrylamide gradient, under reducing (FIG. 15, +βME, lanes 1–7) or non-reducing conditions (−βME, lanes 8 and 9), with no addition (lane 1), addition of mAb 9.3 (5 μg, lane 2), addition of B7Ig (10 μg, lane 3), or addition of chimeric L6 mAb (10 μg, lane 7).

Figure 13:
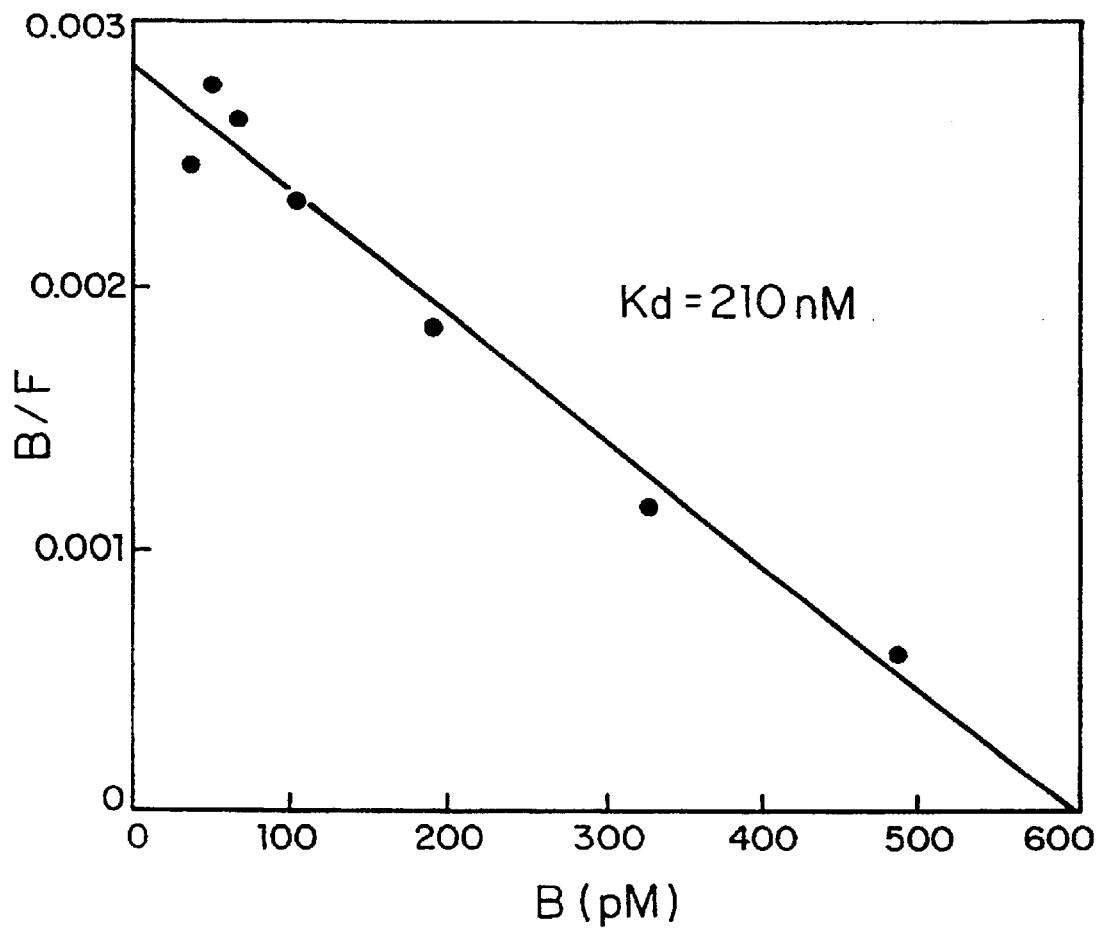
FIG. 13 is a graph showing the results of Scatchard analysis of B7Ig fusion protein binding to immobilized CD28Ig fusion protein as described in Example 3, infra.
Figure 15:
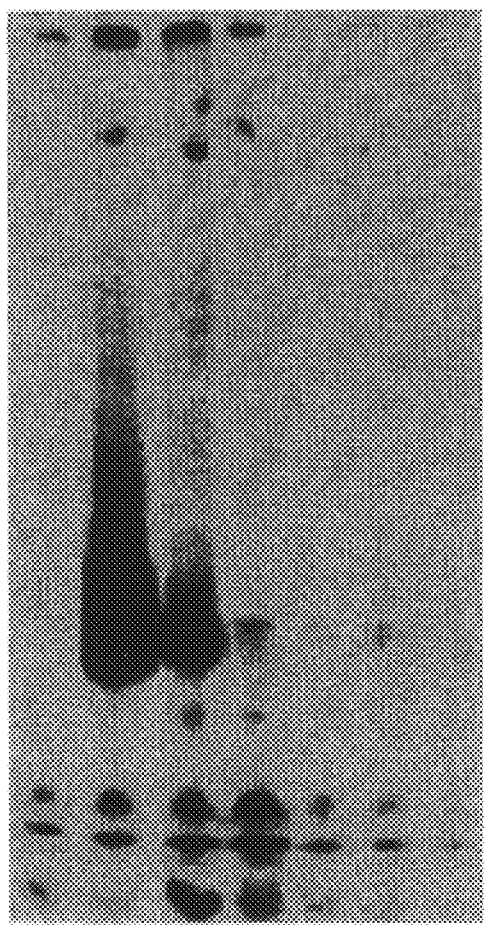
FIG. 15 is an autoradiogram of $^{125}$I-labeled proteins immunoprecipitated by B7Ig as described in Example 3, infra.

As shown in FIG. 15, Both mAb 9.3 and B7Ig immunoprecipitated a protein having a $M_r$ of approximately 45,000 under reducing conditions, and proteins having a $M_r$ of approximately 45,000 and approximately 90,000 under non-reducing conditions, with the latter form being more prominent. The protein having a $M_r$ of approximately 45,000 found in the sample precipitated with chimeric mAb L6 was due to spillover and was not observed in other experiments. mAb 9.3 was more effective at immunoprecipitation than B7Ig, in agreement with the greater affinity of the mAb (FIGS. 12 and 13). Identical results were obtained when CD28$^+$ CHO cells were used for immunoprecipitation analysis. Preclearing of CD28 by immunoprecipitation with mAb 9.3 also removed B7Ig-precipitable material, indicating that both mAb 9.3 and B7Ig bound the same $^{125}$I-labeled protein.

Taken together, the results in these experiments indicate that CD28 is the major receptor for B7Ig on PHA-activated T cells.

Effects of B7 Binding to CD28 on CD28-mediated Adhesion mAbs to CD28 have potent biological activities on T cells, suggesting that interaction of CD28 with its natural ligand(s) may also have important functional consequences. As a first step in determining functional consequences of interaction between B7 and CD28, it was determined whether B7Ig could block the CD28-mediated adhesion assay described above. The adhesion of $^{51}$Cr-labeled PM lymphoblastoid cells to monolayers of CD28$^+$ CHO cells was measured as described above, in the presence of the indicated amounts of mAb 9.3 or B7Ig. Data are expressed in FIG. 16 as a percentage of cells bound in the absence of competitor (40,000 cpm or approximately 1.1×10$^5$ cells). Each point represents the mean of triplicate determinations; coefficients of variation were ≦25%.

Figure 16:
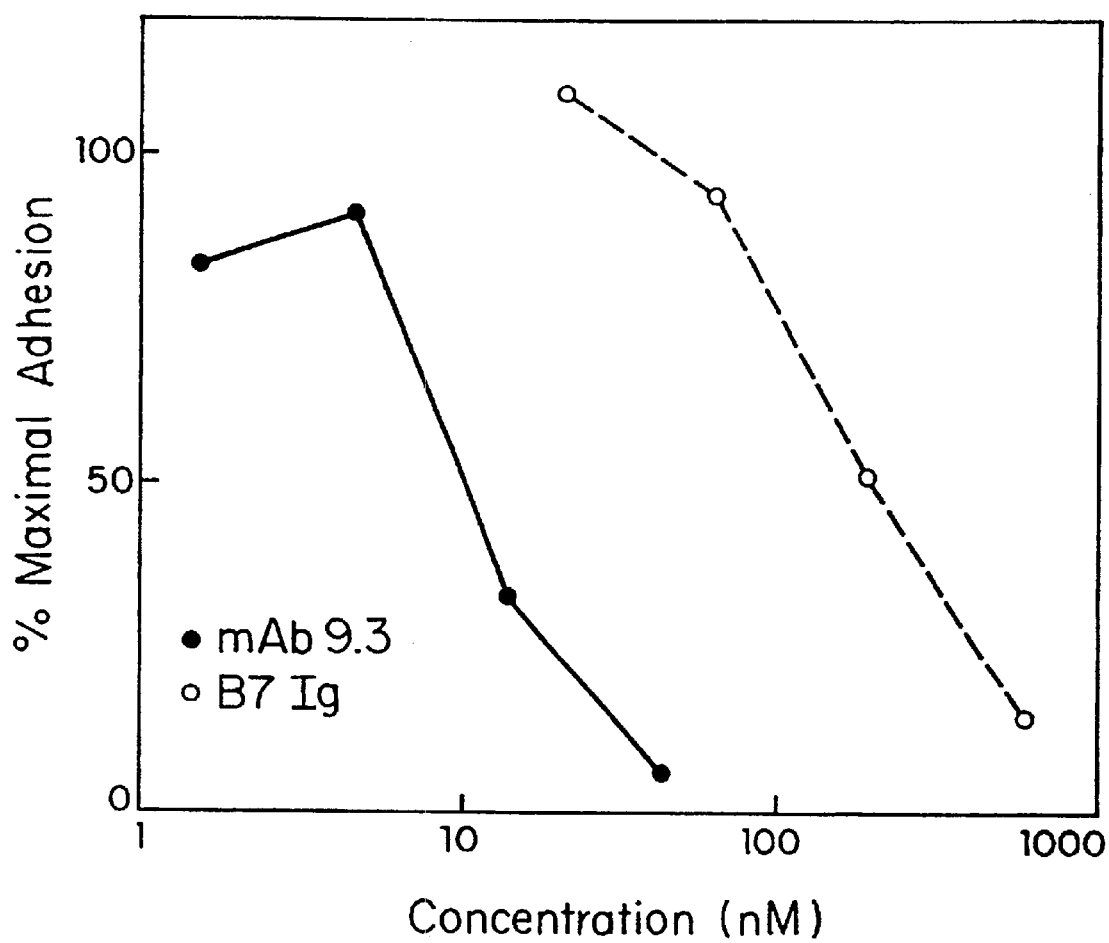
FIG. 16 is a graph showing the effect of B7Ig binding to CD28 on CD28-mediated adhesion as described in Example 3, infra.

As shown in FIG. 16, B7Ig blocked CD28-mediated adhesion somewhat less effectively than mAb 9.3 (half-maximal inhibition at 200 nM as compared with 10 nM for mAb 9.3). The relative effectiveness of these molecules at inhibiting CD28-mediated adhesion was similar to their relative binding affinities in competition binding experiments (FIG. 12). CD28Ig failed to inhibit CD28-mediated adhesion at concentrations of up to 950 nM, suggesting that much higher levels of CD28Ig were required to compete with the high local concentrations of CD28 present on transfected cells.

The Effects of B7 On T Cell Proliferation

It was further investigated whether triggering of CD28 by B7 was costimulatory for T cell proliferation. The ability of B7Ig to costimulate proliferation of PBL together with anti-CD3 was first explored. PBL were isolated and cultured in the presence of the costimulators of T cell proliferation indicated in Table 2. Anti-CD3 stimulation was with mAb G19-4 at 1 μg/ml in solution. For CD28 stimulation, mAb 9.3 or B7Ig were added in solution at 1 μg/ml, or after immobilization on the culture wells by pre-incubation of proteins at 10 μg/ml in PBS for 3 h at 23° C. and then washing the culture wells. B7$^+$ CHO and control dhfr$^+$ CHO cells were irradiated with 1,000 rad before mixing with PBL at a 4:1 ratio of PBL/CHO cells. After culture for 3 d, proliferation was measured by uptake of [$^3$H] thymidine for 5 h. Values shown are means of determinations from quadruplicate cultures (SEM<15%).

In several experiments, B7Ig in solution at concentrations of 1–10 μg/ml showed only a modest enhancement of proliferation even though the anti-CD28 mAb 9.3 was effective. Because CD28 crosslinking has been identified as an important determinant of CD28 signal transduction (Ledbetter et al., *Blood* 75:1531 (1990)), B7Ig was also compared to 9.3 when immobilized on plastic wells (Table 2, Exp. 1).

TABLE 2

| Exp. 1 | CD28 Stimulation | [$^3$H]-T incorporation | |
|---|---|---|---|
| | | − Anti-CD3 | + Anti-CD3 |
| | | cpm × 10$^{-3}$ | |
| 1 | None | 0.1 | 26.0 |
| | mAb 9.3 (soln.) | 0.3 | 156.1 |
| | mAb 9.3 (immob.) | 0.1 | 137.4 |
| | B7Ig (immob.) | 0.1 | 174.5 |
| 2 | None | 0.2 | 19.3 |
| | mAb 9.3 (soln.) | 0.4 | 75.8 |
| | B7 + CHO cells | 9.4 | 113.9 |
| | dhfr + CHO cells | 23.8 | 22.1 |

Under these conditions, B7Ig was able to enhance proliferation and compared favorably with mAb 9.3. B7$^+$ CHO cells also were tested and compared with control dhfr$^+$ CHO cells for costimulatory activity on resting lymphocytes (Table 2, Exp. 2). In this experiment, proliferation was seen with dhfr$^+$ CHO cells in the absence of anti-CD3 mAb because of residual incorporation of [$^3$H]thymidine after irradiation of these cells. The stimulation by dhfr$^+$ cells was not enhanced by anti-CD3 mAb and was not observed in other experiments (Tables 3 and 4) where transfected CHO cells were added at lower ratios.

For the experiments. shown in Table 3, PHA blasts were cultured at 50,000 cells/well with varying amounts of irradiated CH) cell transfectants. After 2 d of culture, proliferation was measured by a 5 h pulse of [$^3$H]thymidine. Shown are means of quadruplicate determinations (SEM<15%). Background proliferation of PHA blasts without added CHO cells was 11,200 cpm. [$^3$H]thymidine incorporation by irradiated B7$^+$ CHO and CD5$^+$CHO cells alone was >1,800 cpm at each cell concentration and was subtracted from the values shown. For the experiments summarized in Table 4, PHA blasts were stimulated as described in Table 3, with irradiated CHO cells at a ratio of 40:1 T cells/CHO cells. mAbs were added at 10 μg/ml at the beginning of culture. mAb LB-1 (Yokochi et al., supra) is an isotype-matched control for mAb BB-1. Proliferation was measured by uptake of [$^3$H]thymidine during a 5 h pulse after 2 d of culture. Values represent means of quadruplicate cultures (SEM<15%).

B7$^+$ CHO cells were very effective at costimulation with anti-CD3 mAb, indicating that cell surface B7 had similar activity in this assay as the anti-CD28 mAbs.

B7$^+$ CHO cells were also tested as to whether they could directly stimulate proliferation of resting PHA blasts which respond directly to CD28 crosslinking by mAb 9.3. Again, the B7$^+$ CHO cells were very potent in stimulating proliferation (Table 3) and were able to do so at very low cell numbers (PHA blast:B7$^+$ CHO ratios of >800:1). The control CD5$^+$ CHO cells did not possess a similar activity. (In a number of different experiments neither dhfr CHO, CD5$^+$ CHO, nor CD7$^+$ CHO cells stimulated T cell proliferation. These were therefore used interchangeably as negative controls for effects induced by B7$^+$ CHO cells. The stimulatory activity of B7$^+$ CHO was further shown to result from CD28/B7 interaction, since mAb BB1 inhibited stimulation by the B7$^+$ CHO cells without affecting background proliferation in the presence of CD7$^+$ CHO cells (Table 4). mAb LB-1 (Yokochi et al., supra), an IgM mAb to a different B cell antigen, did not inhibit proliferation. mAb 9.3 (Fab fragments) inhibited proliferation induced by B7$^+$ CHO and as well as background proliferation seen with CD7$^+$ CHO cells.

TABLE 3

| | [$^3$H]-T incorporation | |
|---|---|---|
| T cells/CHO cells | + B7$^+$ CHO | + CD5$^+$ CHO |
| | cpm × 10$^{-3}$ | |
| 25:1 | 92.7 | 15.5 |
| 50:1 | 135.4 | 19.4 |
| 100:1 | 104.8 | 16.8 |
| 200:1 | 90.3 | 17.7 |
| 400:1 | 57.0 | 13.7 |
| 800:1 | 42.3 | 17.6 |

TABLE 4

| Stimulation | mAb | [$^3$H]-T incorporation cpm × 10$^{-3}$ |
|---|---|---|
| None | None | 10.8 |
| B7$^+$ CHO | None | 180 |
| B7$^+$ CHO | 9.3 Fab | 132 |
| B7$^+$ CHO | BB-1 | 98.3 |
| B7$^+$ CHO | LB-1 | 196 |
| CD7$^+$ CHO | None | 11.5 |
| CD7$^+$ CHO | 9.3 Fab | 10.0 |
| CD7$^+$ CHO | BB-1 | 10.0 |
| CD7$^+$ CHO | LB-1 | 11.3 |

These experiments show that B7 is able to stimulate signal transduction and augment T cell activity by binding to CD28, but that crosslinking is required and B7 expressed on the cell surface is most effective.

The Effects of B7 on IL-2 mRNA Accumulation

Effects of CD28/B7 interactions on IL-2 production were investigated by analyzing transcript levels in PHA-blasts stimulated with B7$^+$ CHO cells or CD7$^+$ CHO cells. RNA was prepared from stimulated cells and tested by RNA blot analysis for the presence of IL-2 transcripts as follows.

Figure 17:
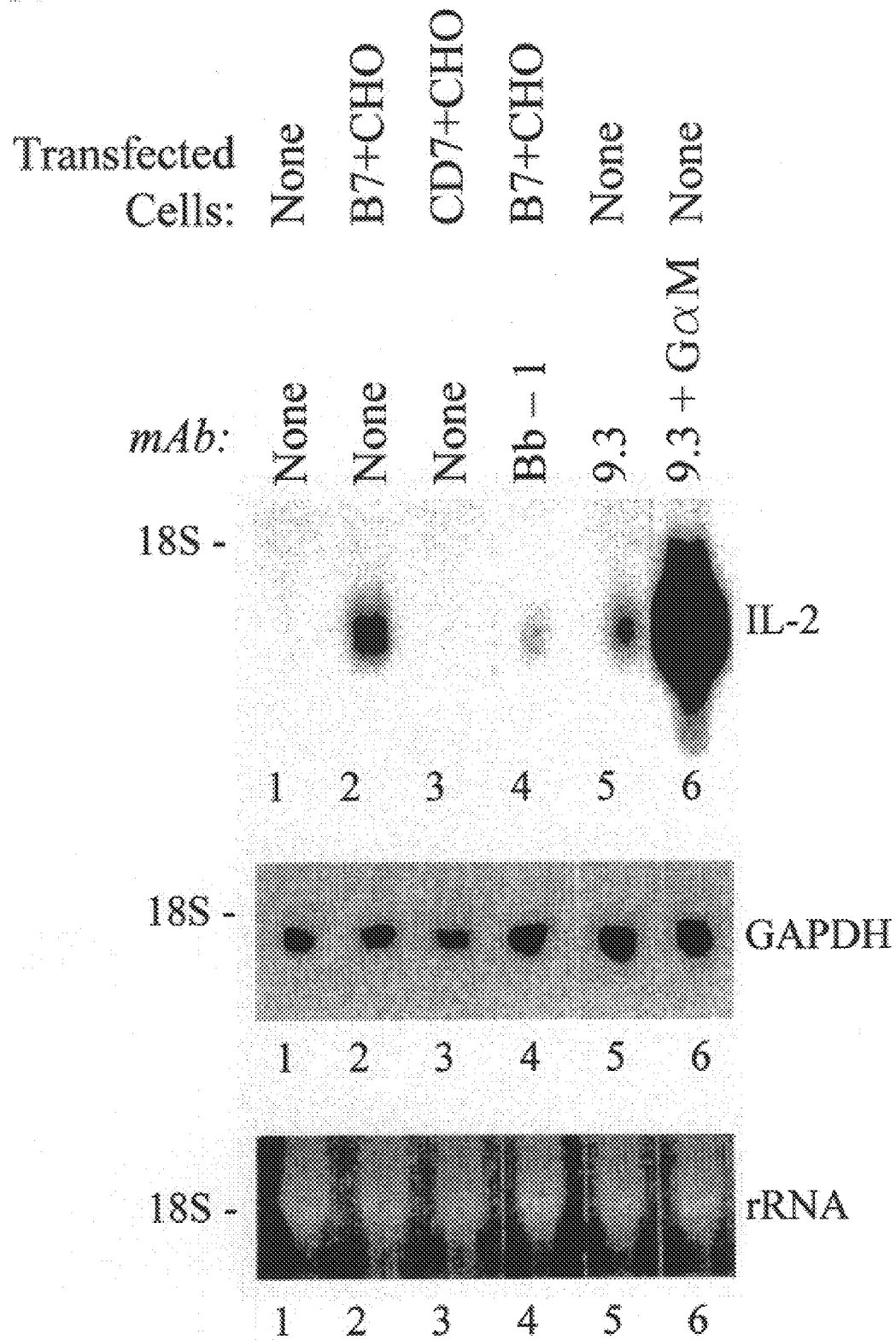
FIG. 17 is a photograph of the results of RNA blot analysis of the effects of B7 on accumulation of IL-2 mRNA as described in Example 3, infra.

PHA blasts (5×10$^7$) were mixed with transfected CHO cells at a ratio of 40:1 T cells/CHO cells, and/or mAbs as indicated in FIG. 17. mAb 9.3 was used at 10 μg/ml. mAb BB-1 was added at 20 μg/ml 1 h before addition of B7$^+$ CHO cells. When mAb 9.3 was crosslinked, goat anti-mouse Ig (40 μg/ml) was added 10 min after addition of mAb 9.3. Cells were incubated for 6 h at 37° C. and RNA was isolated and subjected to RNA blot analysis using $^{32}$P-labeled IL-2 or GAPDH probes as described below.

RNA was prepared from stimulated PHA blasts by the procedure described by Chomczynki and Sacchi, *Anal. Biochem* 162:156 (1987), incorporated by reference herein. Aliquots of RNA (20 μg) were fractionated on formaldehyde agarose gels and then transferred to nitrocellulose by capillary action. RNA was crosslinked to the membrane by UV light in a Stratalinker (Stratagene, San Diego, Calif.), and the blot was prehybridized and hybridized with a $^{32}$P-labeled probe for human IL-2 (prepared from an approximately 600-bp cDNA fragment provided by Dr. S. Gillis; Immunex Corp., Seattle, Wash.). Equal loading of RNA samples was verified both by rRNA staining and by hybridization with a rat glyceraldehyde-6-phosphate dehydrogenase probe (GAPDH, an approximately 1.2-kb cDNA fragment provided by Dr. A Purchio, Bristol-Myers Squibb Pharmaceutical Research Institute, Seattle, Wash.).

As shown in FIG. 17, B7$^+$ CHO cells, but not CD7$^+$ CHO cells, induced accumulation of IL-2 mRNA transcripts. Induction by B7$^+$ CHO cells was partially blocked by TAb BB-1. Induction by B7$^+$ CHO cells was slightly better than achieved by mAb 9.3 in solution, but less effective than mAb 9.3 after crosslinking with goat anti-mouse Ig. Thus, triggering of CD28 by cell surface B7 on apposing cells stimulated IL-2 mRNA accumulation.

The apparent $K_d$ value for the interaction of soluble Ig C$\gamma$ fusions of CD28 and B7 (approximately 200 nM), obtained from the above experiments, is within the range of affinities observed for mAbs (2–10,000 nM; Alzari et al., *Annu. Ref. Immunol.* 6:555 (1988)) and compares favorably with the affinities estimated for other lymphoid adhesion molecules. Schneck et al., (*Cell* 56:47 (1989)) estimated the affinity ($K_d$ approximately 100 nM) between a murine T cell hybridoma TCR and soluble alloantigen (class I MHC molecules). A $K_d$ of 400 nM was measured between CD2 and LFA3 (Recny et al., *J. Biol. Chem.* 265:8542 (1990)). The affinity of CD4 for class II MHC, while not measured directly, was estimated (Clayton et al., *Nature (Lond.)* 339:548 (1989)) to be $\geq 10,000$ times lower than the affinity of gp120-CD4 interactions ($K_d$=4 nM; Lasky et al., *Cell* 50:975 (1987)). Thus, the affinity of B7 for CD28 appears greater than affinities reported for some other lymphoid adhesion systems.

The degree to which the apparent $K_d$ of CD28/B7 interaction reflects their true affinity, as opposed to their avidity, depends on the valency and/or aggregation of the fusion protein preparations. The degree of aggregation of these preparations was examined by size fractionation (TSK G3000SW column eluted with PBS). Under these conditions, B7Ig eluted at $M_r$ approximately 350,000, and CD28Ig at $M_r$ approximately 300,000. Both proteins thus behaved in solution as larger molecules than they appeared by SDS-PAGE (FIG. 10), suggesting that they may form higher aggregates. Alternatively, these results may indicate that both fusion proteins assume extended conformations in solution, resulting in large Stokes radii. Regardless, the interaction that was measured using soluble proteins probably underestimates the true avidity between CD28 and B7 in their native membrane-associated state.

The relative contribution of different adhesion systems to the overall strength of T cell-B cell interactions is not easily gauged, but is likely a function of both affinity/avidity and the densities on apposing cell surfaces of the different receptors and counter-receptors involved. Since both CD28 and B7 are found at relatively low levels on resting lymphoid cells (Lesslauer et al., *Eur. J. Immuno.* 16:1289 (1986); Freeman et al., supra 1989), they may be less involved than other adhesion systems (Springer *Nature (Lond).* 346:425 (1990)) in initiating intercellular interactions. The primary role of CD28/B7 interactions may be to maintain or amplify a response subsequent to induction of these counter-receptors on their respective cell types.

Binding of B7 to CD28 on T cells was costimulatory for T cell proliferation (Tables 2–4) suggesting that some of the biological effects of anti-CD28 mAbs result from their ability to mimic T cell activation resulting from natural interaction between CD28 and its counter-receptor, B7. mAb 9.3 has greater affinity for CD28 than does B7Ig (FIGS. 15 and 16), which may account for the extremely potent biological effects of this mAb (June et al., supra 1989) in costimulating polyclonal T cell responses. Surprisingly, however, anti-CD28 mAbs are inhibitory for antigen-specific T cell responses (Damle et al., *Proc. Natl. Acad. Sci. USA* 78:5096 (1981); Lesslauer et al., supra 1986). This may indicate that antigen-specific T cell responses are dependent upon costimulation via CD28/B7 interactions, and that inhibition therefore results from blocking of CD28 stimulation. Despite the inhibition, CD28 must be bound by mAb under these conditions, implying that triggering by mAb is not always equivalent to triggering by B7. Although mAb 9.3 has higher apparent affinity for CD28 than B7 (FIG. 12), it may be unable under these circumstances to induce the optimal degree of CD28 clustering (Ledbetter et al., supra 1990) for simulation.

CD28/B7 interactions may also be important for B cell activation and/or differentiation. As described above in Example 2, mAbs 9.3 and BB-1 block $T_h$ cell-induced Ig production by B cells. This blocking effect may be due in part to inhibition by these mAbs of production of $T_h$-derived B cell-directed cytokines, but may also involve inhibition of B cell activation by interfering with direct signal transduction via B7. These results suggest that cognate activation of B lymphocytes, as well as $T_h$ lymphocytes, is dependent upon interaction between CD28 and B7.

The above results demonstrate that the ligand for CD28 receptor, the B7 antigen, is expressed on activated B cells and cells of other lineages. These results also show that CD28 receptor and its ligand, B7, play a pivotal role during both the activation of CD4$^+$ $T_h$ cell and $T_h$-induced differentiation of B cells. The inhibition of anti-CD28 and anti-B7 mAbs on the cognate $T_h$:B interaction also provide the basis for employing the CD28Ig and B7Ig fusion proteins, and monoclonal antibodies reactive with these proteins, to treat various autoimmune orders associated with exaggerated B cell activation such as insulin-dependent diabetes mellitus, myasthenia gravis, rheumatoid arthritis and systemic lupus erythematosus (SLE).

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

We claim:

1. A method for inhibiting T cell proliferation resulting from binding of B7 and CD28 comprising contacting CD28 positive T cells with a soluble B7 fusion protein so as to bind CD28 on the CD28 positive T cells with the soluble B7 fusion protein and thereby inhibiting T cell proliferation.

2. The method of claim 1, wherein the soluble B7 fusion protein has an amino acid sequence containing amino acid residues from about position 1 to about position 215 of the amino acid sequence corresponding to the extracellular domain of B7 which recognizes and binds the CD28 positive T cells.

3. The method of claim 1, wherein the soluble B7 fusion protein comprises a fusion polypeptide having a first amino acid sequence corresponding to the extracellular domain of B7 which recognizes and binds CD28 and a second amino acid sequence corresponding to a moiety that alters the solubility, affinity, and/or valency of the soluble B7 fusion protein for binding to CD28.

4. The method of claim 3, wherein the moiety is an immunoglobulin constant region.

5. The method of claim 4, wherein the immunoglobulin constant region is a human immunoglobulin Cγ1 region.

6. The method of claim 1, wherein the soluble B7 fusion protein comprises a fusion polypeptide having a first amino acid sequence containing amino acid residues from about position 1 to about position 215 of the amino acid sequence corresponding to the extracellular domain of the soluble B7 fusion protein which recognizes and binds CD28 and a second amino acid sequence corresponding to the hinge, CH2, and CH3 regions of human immunoglobulin Cγ1.

7. A method for inhibiting the binding of CD28 positive T cells to B7 positive B cells comprising contacting the CD28 positive T cells with a soluble B7 fusion protein which recognizes and binds CD28 on the CD28 positive T cells thereby preventing binding of CD28 to the B7 positive B cells.

8. The method of claim 7, wherein the soluble B7 fusion protein is a B7Ig fusion protein comprising an amino acid sequence containing amino acid residues from about position 1 to about position 215 of the amino acid sequence corresponding to the extracellular domain of B7 which recognizes and binds CD28.

9. The method of claim 8, wherein the fusion protein is B7Ig fusion protein having the amino acid sequence encoded by DNA contained in the plasmid having ATCC No. 68627.

10. A method of inhibiting CD28 positive T cell responses comprising reacting B7 positive B cells with a soluble CD28 fusion protein so as to bind the B7 positive B cells with the soluble CD28 fusion protein thereby inhibiting T cell responses caused by the binding of B7 and CD28.

11. The method of claim 10, wherein the soluble CD28 fusion protein comprises a polypeptide having an amino acid sequence containing amino acid residues from about position 1 to about position 134 of the amino acid sequence corresponding to the extracellular domain of CD28.

12. The method of claim 11, wherein the soluble CD28 fusion protein has a first amino acid sequence corresponding to the extracellular domain of CD28 and a second amino acid sequence corresponding to a moiety that alters the solubility, affinity, and/or valency of the CD28 for binding to B7 positive B cells.

13. The method of claim 12, wherein the moiety is an immunoglobulin constant region.

14. The method of claim 13, wherein the immunoglobulin constant region is a human immunoglobulin Cγ1 region.

15. The method of claim 10, wherein the soluble CD28 fusion protein comprises a polypeptide having a first amino acid sequence containing amino acid residues from about position 1 to about position 134 of the amino acid sequence corresponding to the extracellular domain of CD28 and a second amino acid sequence corresponding to the hinge, CH2, and CH3 regions of human immunoglobulin Cγ1.

16. The method of claim 15, wherein the fusion protein is CD28Ig fusion protein having the amino acid sequence encoded by DNA contained in the plasmid having ATCC No. 68628.

* * * * *